United States Patent
Stahl et al.

(10) Patent No.: US 11,471,703 B2
(45) Date of Patent: *Oct. 18, 2022

(54) SYSTEMS AND METHODS FOR PULSE PARAMETER MODULATION

(71) Applicant: UIH-RT US LLC, Walnut Creek, CA (US)

(72) Inventors: Johannes Stahl, Houston, TX (US); Jonathan Maltz, Houston, TX (US)

(73) Assignee: UIH-RT US LLC, Walnut Creek, CA (US)

( * ) Notice: Subject to any disclaimer, the term of this patent is extended or adjusted under 35 U.S.C. 154(b) by 234 days.

This patent is subject to a terminal disclaimer.

(21) Appl. No.: 16/872,288

(22) Filed: May 11, 2020

(65) Prior Publication Data
US 2020/0269069 A1  Aug. 27, 2020

Related U.S. Application Data

(63) Continuation of application No. 15/690,363, filed on Aug. 30, 2017, now Pat. No. 10,646,729.

(51) Int. Cl.
*A61N 5/10* (2006.01)
*G16H 20/40* (2018.01)
(Continued)

(52) U.S. Cl.
CPC ........... *A61N 5/1038* (2013.01); *A61N 5/103* (2013.01); *A61N 5/1048* (2013.01);
(Continued)

(58) Field of Classification Search
CPC ........ A61N 5/103–1039; A61N 5/1039–1084; A61N 2005/1041; A61N 2005/1085–1098
See application file for complete search history.

(56) References Cited

U.S. PATENT DOCUMENTS

| 7,672,428 B1 | 3/2010 | Brown et al. |
| 2010/0187435 A1 | 7/2010 | Iseki et al. |

(Continued)

FOREIGN PATENT DOCUMENTS

| CN | 103845816 A | 6/2014 |
| CN | 105807306 | 7/2016 |

OTHER PUBLICATIONS

First Office Action in Chinese Application No. 201811005980.9 dated Mar. 4, 2020, 17 pages.

*Primary Examiner* — Thaddeus B Cox
(74) *Attorney, Agent, or Firm* — Metis IP LLC

(57) ABSTRACT

The present disclosure relates to systems and methods for pulse parameter modulation. The systems may perform the methods to obtain information related to a treatment plan; determine a backward window based on the information related to the treatment plan, within which one or more radiation pulses have been transmitted; determine backward information associated with the backward window based on the information related to the treatment plan and the backward window; determine a forward window based on the information related to the treatment plan, within which one or more radiation pulses are to be transmitted; determine forward information associated with the forward window based on the information related to the treatment plan, the backward information, and the forward window; and determine one or more pulse parameters of the forward window based on the forward information.

20 Claims, 14 Drawing Sheets

(51) Int. Cl.
  *G16H 30/20*    (2018.01)
  *G16H 40/63*    (2018.01)

(52) U.S. Cl.
  CPC ........... *A61N 5/1071* (2013.01); *G16H 20/40* (2018.01); *G16H 30/20* (2018.01); *G16H 40/63* (2018.01)

(56) References Cited

U.S. PATENT DOCUMENTS

| | | |
|---|---|---|
| 2012/0160996 A1 | 6/2012 | Jongen |
| 2013/0324784 A1 | 12/2013 | Fredriksson |
| 2018/0078786 A1 | 3/2018 | Vik et al. |
| 2018/0272155 A1 | 9/2018 | Thieme et al. |
| 2018/0304099 A1 | 10/2018 | Li et al. |

SYSTEMS AND METHODS FOR PULSE PARAMETER MODULATION

CROSS-REFERENCE TO RELATED APPLICATIONS

This application is a continuation of U.S. patent application Ser. No. 15/690,363, now U.S. Pat. No. 10,646,729, filed on Aug. 30, 2017, the contents of which are incorporated herein by reference to its entirety.

TECHNICAL FIELD

The present disclosure generally relates to systems and methods for modulating radiation dose delivery, and more particularly, to systems and methods for modulating pulse parameters in a radiation treatment.

BACKGROUND

Radiation therapy or radiotherapy, often abbreviated as RT, RTx, or XRT, is a therapy applied in cancer treatment to control or kill malignant cells and normally delivered by a linear accelerator (linac), particle accelerator, or radioactive source (teletherapy). RT is also used in treating many other medical conditions, including those where control of the immune system and inflammation is required. Historically, radiotherapy devices such as medical linear accelerators have employed several fixed radiation output rates when delivering treatments. In modern dynamic arc treatments, output rates and the motion of system components such as the accelerator gantry and collimators may be synchronized so that the planned dose is delivered as the mechanical configuration of the machine is continuously adapted to be consistent with the treatment plan. At present, all linear accelerators in use for external beam radiation therapy operate in relatively low duty cycle pulsed mode (e.g., pulse widths of the order of $\frac{1}{1000}$th of a pulse repetition period). Also, variation exists between the radiation output contained in each pulse. This may lead to inaccuracies in the amount of output radiation dose delivered during a specific time period, and also to wild fluctuations in the reported instantaneous radiation output rate, if this quantity is not smoothed over a time window containing many pulses. Since output rate is used not only to provide an indication to the user of current output rate, but also for feedback purposes and to trigger error conditions (treatment interlocks), having a stable measurement of output rate is critical to system performance. Often, the smoothing window chosen to stabilize the output rate measurement is arbitrary and non-adaptive to the current delivery conditions as specified in the treatment plan. Therefore, it is desirable to provide systems and methods for pulse parameter (amplitude, pulse shape, pulse energy, pulse period and duty cycle) modulation to reduce or eliminate the inaccuracies and fluctuations in output radiation.

SUMMARY

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

According to a first aspect of the present disclosure, a system may include one or more storage media and one or more processors configured to communicate with the one or more storage media. The one or more storage media may include a set of instructions for modulating one or more pulse parameters. When the one or more processors executing the set of instructions, the one or more processors may be directed to perform one or more of the following operations. The one or more processors may obtain information related to a treatment plan. The one or more processors may determine a backward window based on the information related to the treatment plan, within which one or more radiation pulses have been transmitted. The one or more processors may determine backward information associated with the backward window based on the information related to the treatment plan and the backward window. The one or more processors may determine a forward window based on the information related to the treatment plan, within which one or more radiation pulses are to be transmitted. The one or more processors may determine forward information associated with the forward window based on the information related to the treatment plan, the backward information, and the forward window. The one or more processors may determine one or more pulse parameters of the forward window based on the forward information.

In some embodiments, the information related to the treatment plan may include at least one of a total time of a treatment, a total radiation during the total time of the treatment, one or more control time points within the total time of the treatment, a radiation output rate associated with each of the one or more control time points within the total time of the treatment, a radiation output per pulse, a cumulative radiation associated with each of the one or more control time points within the total time of the treatment, or an interval between each two neighboring control time points within the total time of the treatment.

In some embodiments, the backward information may include at least one of a backward total radiation of the backward window, a backward cumulative radiation dose of the backward window, a backward interval of the backward window, a backward number of pulses in the backward window, or a backward radiation output per pulse of the backward window.

In some embodiments, to determine the forward information, the one or more processors may determine a first forward interval of the forward window based on the information related to the treatment plan. The one or more processors may determine a forward cumulative radiation dose based on the information related to the treatment plan. The one or more processors may determine a first forward radiation dose based on the forward cumulative radiation dose. The one or more processors may determine a first forward number of pulses in the forward window based on the backward radiation output per pulse and the first forward radiation dose.

In some embodiments, to determine the forward information, the one or more processors may determine whether the first forward interval is less than a first threshold. The one or more processors may determine whether the first forward radiation dose is greater than a second threshold in response to a determination that the first forward interval is greater than or equal to the first threshold.

In some embodiments, to determine the forward information, the one or more processors may determine a second forward radiation dose by modifying the first forward radiation dose based on the second threshold in response to a determination that the first forward radiation dose is greater than the second threshold. The one or more processors may determine a second forward interval based on the second forward radiation dose and the information related to the treatment plan. The one or more processors may determine a second forward number of pulses based on the second forward radiation dose and the backward radiation per pulse.

In some embodiments, to determine the forward information, the one or more processors may determine whether the first forward number of pulses is less than a third threshold in response to a determination that the first forward radiation dose is less than or equal to the second threshold. The one or more processors may determine a third forward number of pulses by modifying the first forward number of pulses based on the third threshold in response to a determination that the first forward number of pulses is less than the third threshold. The one or more processors may determine a third forward interval based on the third forward number of pulses and the information related to the treatment plan.

In some embodiments, the one or more pulse parameters of the forward window may include at least one of pulse energy, a pulse period, a pulse duty cycle, a pulse shape, or a pulse amplitude.

In some embodiments, to determine the one or more pulse parameters of the forward window, the one or more processors may determine the pulse period of the forward window based on a fourth forward interval and a fourth forward number of pulses.

In some embodiments, to determine the one or more pulse parameters of the forward window, the one or more processors may determine whether the pulse period is less than a fourth threshold. The one or more processors may determine a modified pulse period based on the fourth threshold in response to a determination that the pulse period is less than the fourth threshold.

According to a second aspect of the present disclosure, a method may include one or more of the following operations. One or more processors may obtain information related to a treatment plan. The one or more processors may determine a backward window based on the information related to the treatment plan, within which one or more radiation pulses have been transmitted. The one or more processors may determine backward information associated with the backward window based on the information related to the treatment plan and the backward window. The one or more processors may determine a forward window based on the information related to the treatment plan, within which one or more radiation pulses are to be transmitted. The one or more processors may determine forward information associated with the forward window based on the information related to the treatment plan, the backward information, and the forward window. The one or more processors may determine one or more pulse parameters of the forward window based on the forward information.

According to a third aspect of the present disclosure, a non-transitory computer readable medium may comprise at least one set of instructions for modulating one or more pulse parameters. The at least one set of instructions may be executed by one or more processors of a computer server. The one or more processors may obtain information related to a treatment plan. The one or more processors may determine a backward window based on the information related to the treatment plan, within which one or more radiation pulses have been transmitted. The one or more processors may determine backward information associated with the backward window based on the information related to the treatment plan and the backward window. The one or more processors may determine a forward window based on the information related to the treatment plan, within which one or more radiation pulses are to be transmitted. The one or more processors may determine forward information associated with the forward window based on the information related to the treatment plan, the backward information, and the forward window. The one or more processors may determine one or more pulse parameters of the forward window based on the forward information.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "module," and/or "block" used herein are one method to distinguish different components, elements, parts, section or assembly of different level in ascending order. However, the terms may be displaced by other expression if they achieve the same purpose.

Figure 2:
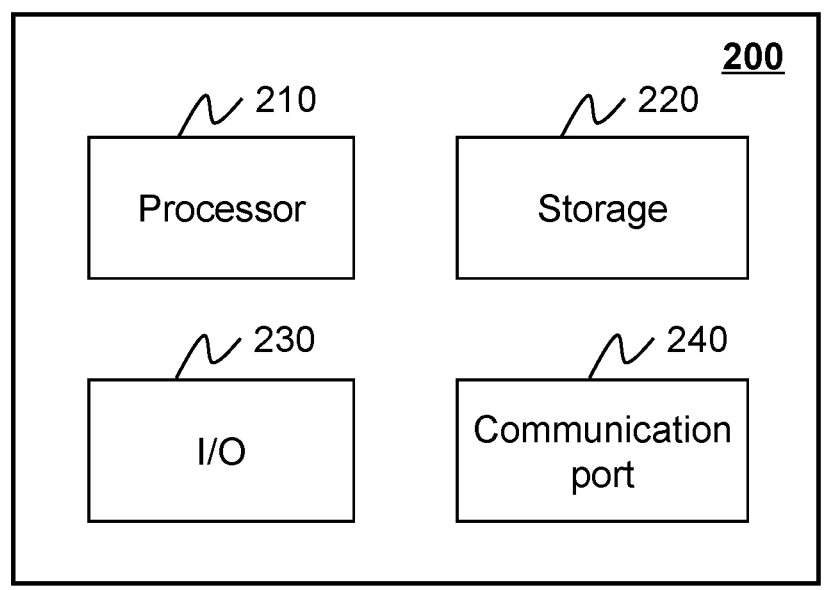
FIG. 2 is a schematic diagram illustrating exemplary hardware and/or software components of an exemplary computing device according to some embodiments of the present disclosure.

Generally, the word "module," or "block," as used herein, refers to logic embodied in hardware or firmware, or to a collection of software instructions. A module, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., the processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an Electrically Programmable Read-Only-Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a module or block is referred to as being "connected to," or "coupled to," another module, or block, it may be directly connected or coupled to, or communicate with the other module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

In the exposition below, the term "pulse period" is used as shorthand for "pulse period and interpulse delay", with the understanding that in the case of linear accelerators, modulation of the interpulse delay is the primary method for control of output rate during a particular treatment fraction, arc, sub-arc, beam or segment.

The term "radiation output" refers to radiation output by the radiation source. Radiation output is measured in Monitor Units (MU). Radiation dose is delivered to volumes upon which the radiation beam is incident. Pulse parameter modulation may be performed based on radiation output, or radiation dose, or a combination of these. Radiation dose to a patient may be measured using a dosimeter place in or on the patient, through simulation of the incident beam and energy deposited in the patient, or via exit dosimetry, in which the beam exiting the patient is measured and the dose to the patient is inferred therefrom. We use the terms "dose" and "output" interchangeably, since either or both may be employed for the teachings contained in the present disclosure.

When we refer to "treatment beam", we refer also to beams generated by the accelerator or other source that are used to image, rather than treat, the patient.

Provided herein are systems and methods for pulse parameter modulation in delivering radiation dose during a radiation therapy/treatment. In some embodiments, a pulse parameter modulation system may modulate one or more pulse parameters to control the output radiation at different times. The pulse parameter modulation system may obtain information related to pulses that have been delivered, determine information related to pulses that are to be delivered (e.g., the number of the pulses that are to be delivered and the time over which the pluses will occur) based on the information related to pulses that have been delivered, and determine the pulse parameters of pulses that are to be delivered based on the information related to pulses that have been delivered.

Figure 1:
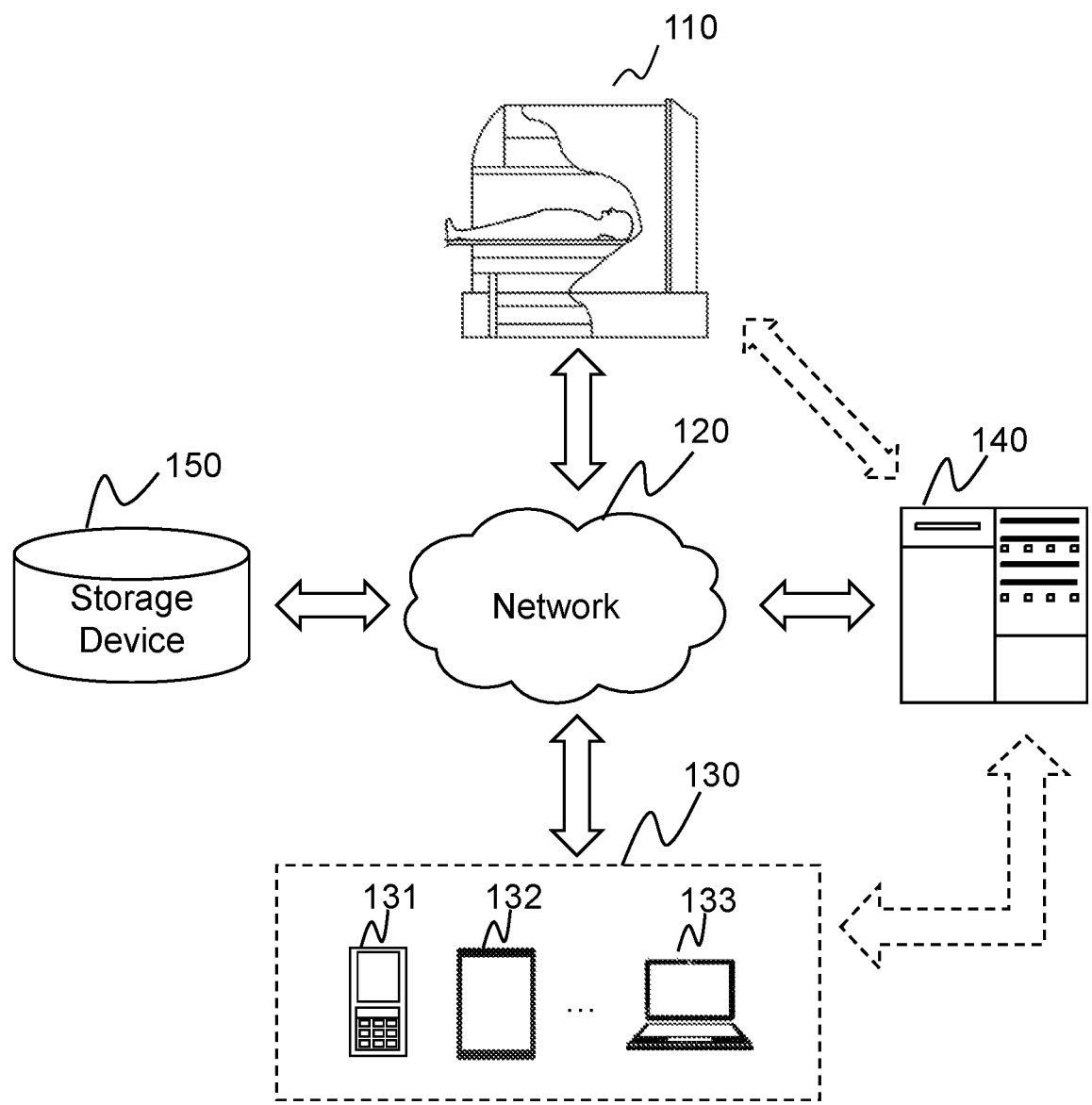
FIG. 1 is a schematic diagram illustrating an exemplary pulse parameter modulation system 100 according to some embodiments of the present disclosure.

FIG. 1 is a schematic diagram illustrating an exemplary pulse parameter modulation system 100 according to some embodiments of the present disclosure. As shown in FIG. 1, the pulse parameter modulation system 100 may include a radiation device 110, a network 120, one or more terminals 130, a server 140, and a storage device 150.

The radiation device 110 may emit radioactive rays to a subject (e.g., a patient). The radioactive rays may include α rays, β rays, γ rays, X rays, neutrons, etc. In some embodiments, the radiation device 110 may emit radioactive rays in a form of radiation pulses. The radiation device 110 may include a medical imaging device such as an X-ray device, a computed tomography (CT) device, a positron emission computed tomography (PET), and a radiotherapy device such as a medical linear accelerator, a Cobalt-60 device, a Gamma knife, X knife, a proton accelerator, a brachytherapy device.

For brevity, the description of the methods and/or systems for pulse parameter modulation in this disclosure may be applied in a radiation therapy/treatment. It should be noted that the description of the methods and/or systems for pulse parameter modulation applied in the radiation therapy is merely provided for the purposes of illustration, and not intended to limit the scope of the present disclosure. For persons having ordinary skills in the art, multiple variations and modifications may be made under the teachings of the present disclosure. For example, the description of the methods and/or systems for pulse parameter modulation in this disclosure may be applied in medical imaging (e.g., CT imaging, PET imaging, X-ray imaging, etc.). However, those variations and modifications do not depart from the scope of the present disclosure.

The radiation therapy may include an external radiation therapy, a Brachytherapy, an intraoperative radiotherapy, a radioisotope therapy, a deep inspiration breath-hold (DIBH), etc. The external beam radiation therapy may include a conventional external beam radiation therapy (2DXRT), a stereotactic radiation therapy (e.g., a stereotactic radiosurgery, a stereotactic body radiation therapy, etc.), a virtual simulation and three-dimensional conformal radiation therapy (3DCRT), an intensity-modulated radiation therapy (IMRT), a volumetric modulated arc therapy (VMAT), a particle therapy, an Auger therapy (AT), etc. The radiation therapy may be used to treat a cancer or a tumor. The tumor may be in a lung, a brain, a spine, a tissue, a prostate, a breast, a cervix, an area of skin, or the like of a body.

The network 120 may include any suitable network that can facilitate exchange of information and/or data for the pulse parameter modulation system 100. In some embodiments, one or more components of the pulse parameter modulation system 100 (e.g., the radiation device 110, the terminal 130, the server 140, the storage device 150, etc.) may communicate information and/or data with one or more other components of the pulse parameter modulation system 100 via the network 120. For example, the server 140 may obtain information related to radioactive rays from the radiation device 110 via the network 120. As another example, the server 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the pulse parameter modulation system 100 may be connected to the network 120 to exchange data and/or information.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the server 140.

The server 140 may process data and/or information obtained from the radiation device 110, the terminal 130, and/or the storage device 150. For example, the server 140 may continuously modulate the pulse parameter to make information related to delivered pulses (e.g., a radiation output rate, a cumulative radiation dose, etc.) be consistent with a treatment plan. In some embodiments, the server 140 may be a single server or a server group. The server group may be centralized or distributed. In some embodiments, the server 140 may be local or remote. For example, the server 140 may access information and/or data stored in the radiation device 110, the terminal 130, and/or the storage device 150 via the network 120. As another example, the server 140 may be directly connected to the radiation device 110, the terminal 130 and/or the storage device 150. In some embodiments, the server 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the server 140 may be implemented by a computing device 200 having one or more components as illustrated in FIG. 2.

The storage device 150 may store data, instructions, and/or any other information. In some embodiments, the storage device 150 may store data obtained from the terminal 130 and/or the server 140. In some embodiments, the storage device 150 may store data and/or instructions that the server 140 may execute or use to perform exemplary methods described in the present disclosure. In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the pulse parameter modulation system 100 (e.g., the server 140, the terminal 130, etc.). One or more components in the pulse parameter modulation system 100 may access the data or instructions stored in the storage device 150 via the network 120. In some embodiments, the storage device 150 may be directly connected to or communicate with one or more other components in the pulse parameter modulation system 100 (e.g., the server 140, the terminal 130, etc.). In some embodiments, the storage device 150 may be part of the server 140.

FIG. 2 is a schematic diagram illustrating exemplary hardware and/or software components of an exemplary computing device 200 on which the server 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the server 140 in accordance with techniques described herein. The computer instructions may include, for example, routines, programs, objects, components, data structures, procedures, modules, and functions, which perform particular functions described herein. For example, the processor 210 may process image data obtained from the radiation device 110, the terminal 130, the storage device 150, and/or any other component of the pulse parameter modulation system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both step X and step Y, it should be understood that step X and step Y may also be performed by two or more different processors jointly or separately in the computing device 200 (e.g., a first processor executes step X and a second processor executes step Y, or the first and second processors jointly execute steps X and Y).

The storage 220 may store data/information obtained from the radiation device 110, the terminal 130, the storage device 150, and/or any other component of the pulse parameter modulation system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the server 140 for determining one or more pulse parameters.

The I/O 230 may input and/or output signals, data, information, etc. In some embodiments, the I/O 230 may enable a user interaction with the server 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the server 140 and the radiation device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with digital imaging and communications in medicine (DICOM) protocol.

Figure 3:
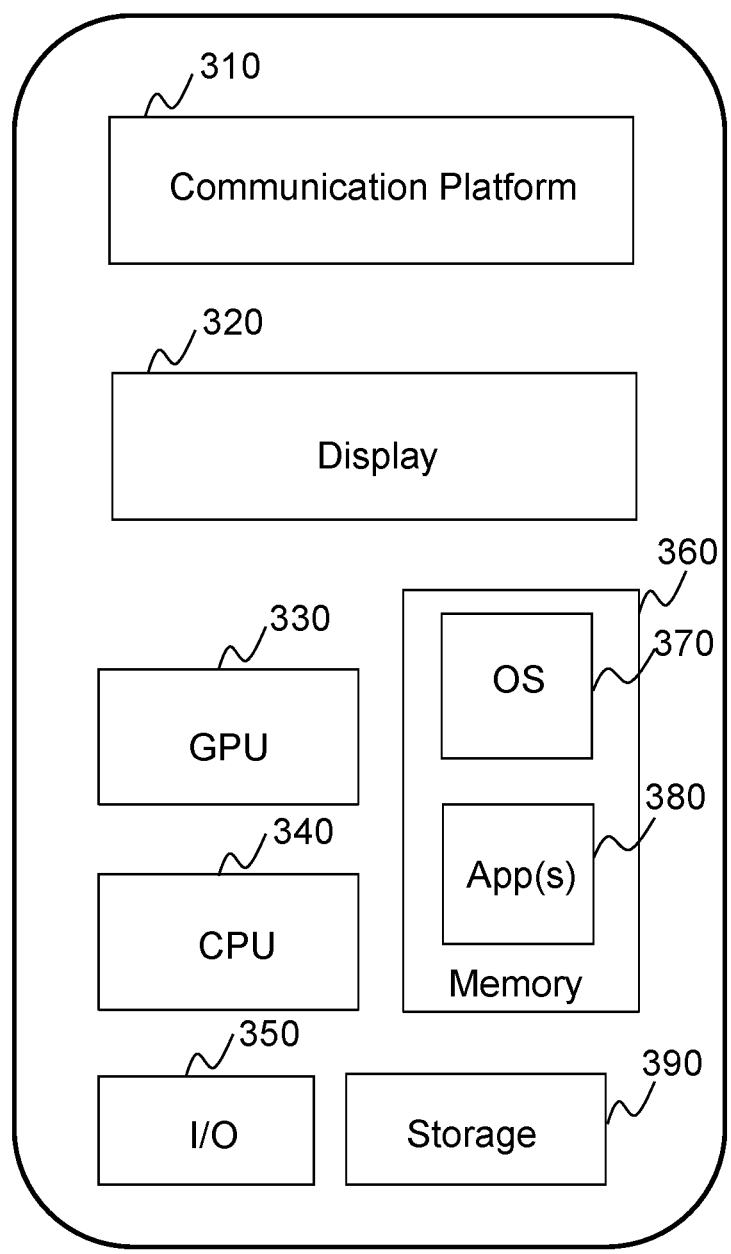
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the server 140. User interactions with the information stream may be achieved via the I/O 350 and provided to the server 140 and/or other components of the pulse parameter modulation system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
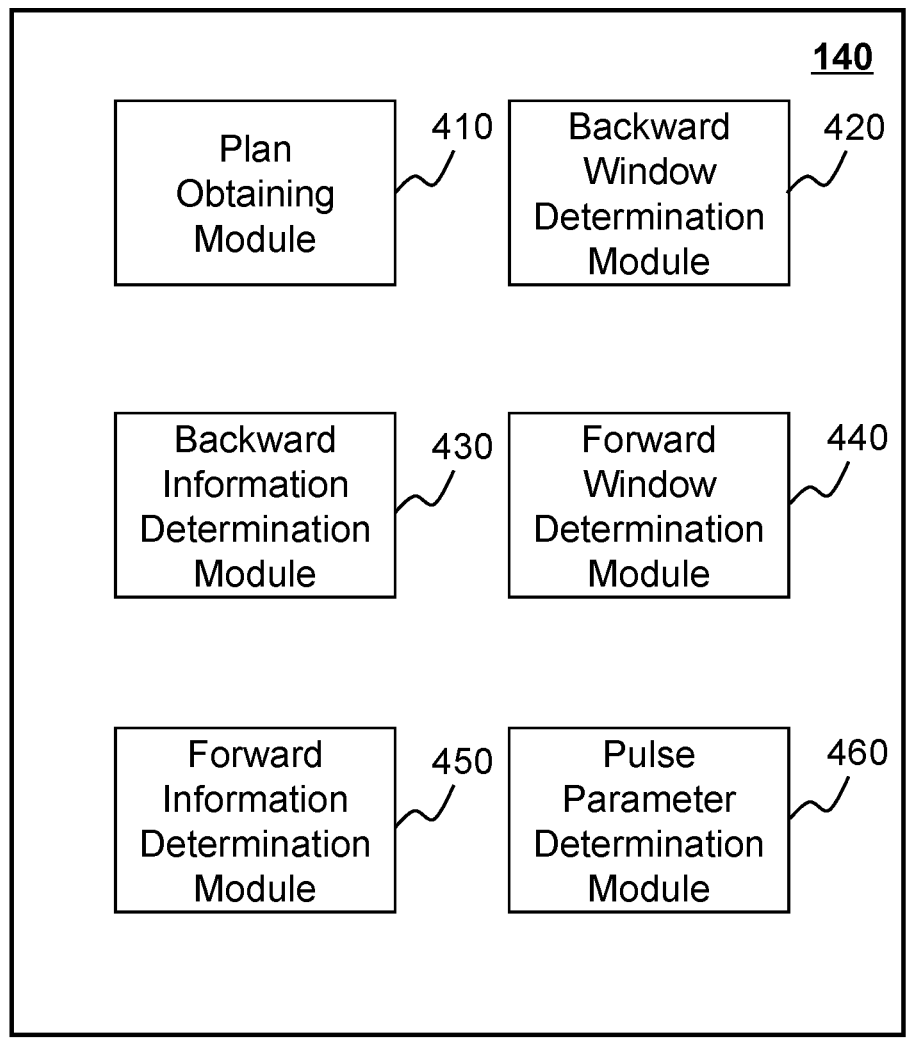
FIG. 4 is a block diagram illustrating an exemplary pulse parameter modulation system according to some embodiments of the present disclosure.

FIG. 4 is a block diagram illustrating an exemplary pulse parameter modulation system according to some embodiments of the present disclosure. In some embodiments, the pulse parameter modulation system 100 may include a plan obtaining module 410, a backward window determination module 420, a backward information determination module 430, a forward window determination module 440, a forward information determination module 450 and a pulse parameter determination module 460.

The plan obtaining module 410 may be configured to obtain information related to a treatment plan (By "information related to the treatment plan", we include actual measured physical information, in the backward window, of the output or dose measured as delivered during the current treatment, or indeed of any other measured system parameters measured or inferred, as prevailing during the backward window). In some embodiments, the information related to the treatment plan may include a total time of a treatment, one or more control time points within the total time of the treatment, a total radiation dose during the total time of the treatment, a cumulative radiation dose associated with each of the one or more control time points, an interval between each two neighboring control time points within the total time of the treatment, a radiation output rate associated with each of the one or more control time points, a radiation output per pulse, or the like, or any combination thereof. A cumulative radiation output associated with a control time point may refer to a radiation output delivered in response to one or more pulses during a time period from the start time of the treatment to the control time point. A control time point may refer to a time point within the total time of the treatment.

The backward window determination module 420 may be configured to determine a backward window. The backward window may refer to a time window prior to the current treatment stage. The backward window may include a plurality of pulses that have been delivered. The backward window may include information related to a part of the treatment prior to the time point that the treatment currently proceeds to. For example, if the user sets four control time points (e.g., $P_1$, $P_2$, $P_3$, and $P_4$) in the treatment plan, and the treatment currently proceeds to time point $P_3$. The time window from time point $P_2$ to time point $P_3$ during which the part of the treatment were performed may be referred to as a backward window.

The backward information determination module 430 may be configured to determine backward information associated with the backward window. The backward information may include the actual recorded information relating to pulses that have been delivered in the backward window. The backward information may include a backward start time of the backward window, a backward end time of the backward window, a radiation output rate of the backward window, a backward total radiation dose of the backward window, a backward cumulative radiation output in the backward window, a backward interval of the backward window, a backward number of pulses in the backward window, a backward radiation dose per radiation pulse of the backward window, or the like, or any combination thereof. The radiation output rate of the backward window may refer to a radiation output per unit time (e.g., per minute, per second, etc.) delivered in the backward window. The backward total radiation dose may refer to a radiation dose delivered in response to the plurality of pulses during the backward interval of the backward window. The backward cumulative radiation dose may refer to a cumulative radiation dose associated with a backward end time of the backward window. The backward cumulative radiation dose may refer to a radiation dose delivered in response to the plurality of pulses during a time period from the start time of the treatment to the backward end time. The backward number of pulses may refer to the number of pulses delivered during the backward interval.

The forward window determination module 440 may be configured to determine a forward window. The forward window may refer to a time window after the current treatment stage. The forward window may include a plurality of pulses that are to be transmitted. The forward window may include information related to a part of the treatment after the time point that the treatment currently proceeds to. For example, if the user sets four control time points (e.g., $P_1$, $P_2$, $P_3$, and $P_4$) in the treatment plan, and the treatment currently proceeds to $P_3$, the time window from time point $P_3$ to time point $P_4$ during which the part of the treatment will be performed may be referred to as a forward window.

The forward information determination module 450 may be configured to determine forward information in the forward window. The forward information may include predicted or planned information relating to pulses that are to be transmitted in the forward window. The forward information may include a forward start time of the forward window, a forward end time of the forward window, a forward interval of the forward window, a forward cumulative radiation dose of the forward window, a forward total radiation dose of the forward window, a forward number of pulses in the forward window, or the like, or any combination thereof. The forward total radiation dose may refer to a radiation dose delivered in response to the plurality of pulses during the forward interval of the forward window. The forward cumulative radiation dose may refer to a cumulative radiation dose associated with the forward end time of the forward window. The forward cumulative radiation dose may refer to a radiation dose delivered in response to the plurality of pulses from the start time of the treatment to the forward end time. The forward number of pulses may refer to the number of pulses delivered during the forward interval.

The pulse parameter determination module 460 may be configured to determine one or more pulse parameters of the forward window based on the forward information. The one or more pulse parameters of the forward window may include at least one of pulse energy, a pulse period, a pulse duty cycle, a pulse shape, or a pulse amplitude. The pulse period of the forward window may refer to an interval between each two neighboring pulses delivered in the forward window.

The modules in the server 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units. For example, the backward window determination module 420 may be integrated in the forward window determination module 440 as a single module which may both determine the backward window and the forward window.

It should be noted that the above description of the pulse parameter modulation system 100 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the server 140 may further include a storage module (not shown in FIG. 4). The storage module may be configured to store data generated during any process performed by any component of in the server 140. As another example, each of components of the server 140 may include a storage device. Additionally or alternatively, the components of the server 140 may share a common storage device.

Figure 5:
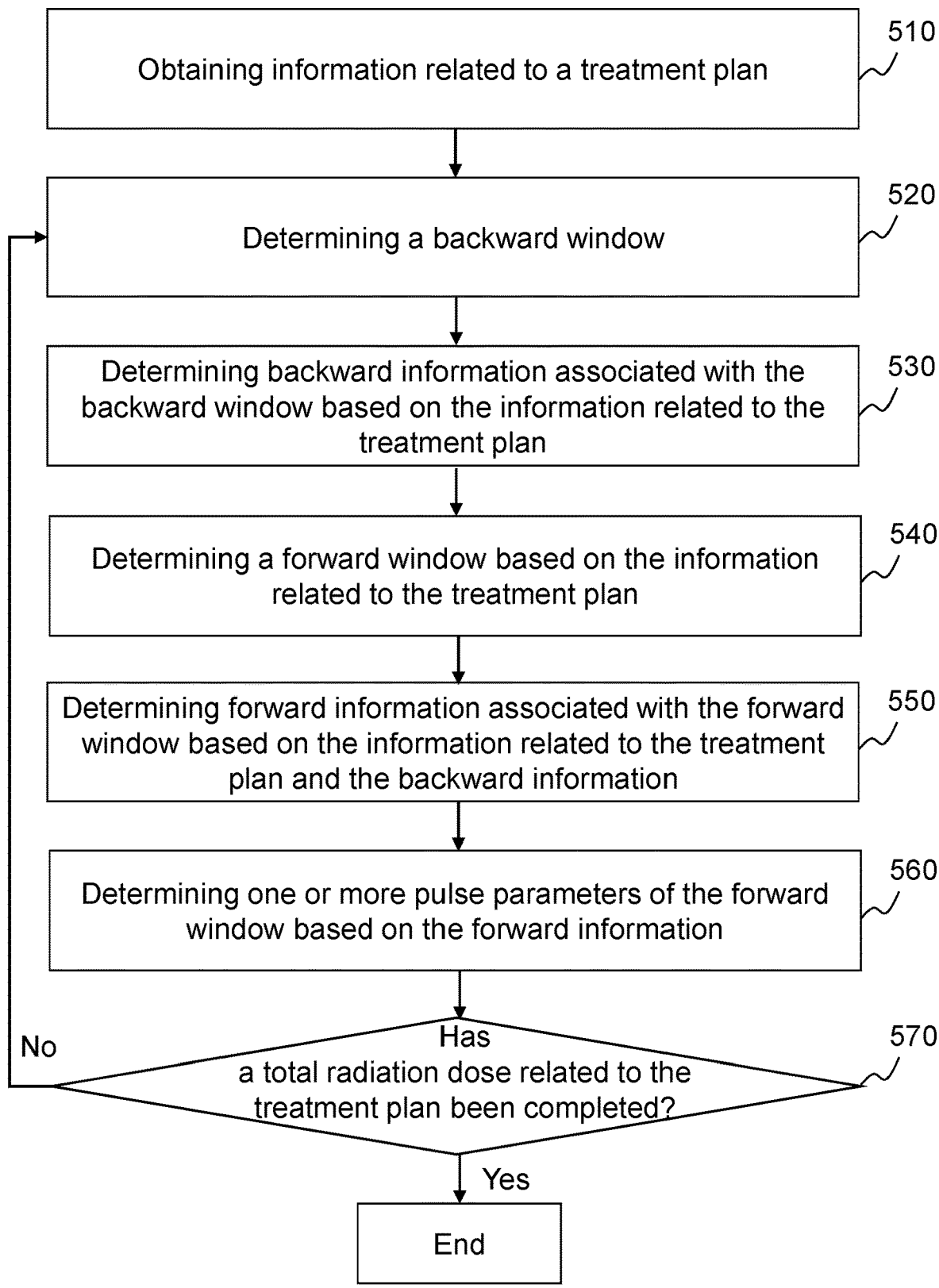
FIG. 5 is a flowchart illustrating an exemplary process for determining one or more pulse parameters of a forward window according to some embodiments of the present disclosure.

FIG. 5 is a flowchart illustrating an exemplary process/method 500 for determining a pulse parameter of a forward window according to some embodiments of the present disclosure. In some embodiments, the process/method 500 may be implemented in the system 100 illustrated in FIG. 1. For example, the process/method 500 may be stored in the storage device 150 and/or a storage device (e.g., the storage 220 of the server 140, the storage 390 of the terminal 130, the memory 360 of the terminal 130, etc.) as a form of instructions, and invoked and/or executed by the server 140 (e.g., the processor 210 of the server 140, or one or more modules in the server 140 illustrated in FIG. 4) and/or the terminal 130 (e.g., the CUP 340 of the terminal 130, or the GPU 330 of the terminal 130). The operations of the illustrated process/method presented below are intended to be illustrative. In some embodiments, the process/method 500 may be accomplished with one or more additional operations not described, and/or without one or more of the operations discussed. Additionally, the order in which the operations of the process/method 500 as illustrated in FIG. 5 and described below is not intended to be limiting.

In 510, the plan obtaining module 410 may obtain information related to a treatment plan. In some embodiments, the information related to the treatment plan may include a total time of a treatment, one or more control time points within the total time of the treatment, a total radiation dose during the total time of the treatment, a cumulative radiation dose associated with each of the one or more control time points, an interval between each two neighboring control time points within the total time of the treatment, a radiation output rate associated with each of the one or more control time points, a radiation output per pulse, or the like, or any combination thereof. In some embodiments, the interval between each two neighboring control time points within the total time of the treatment may be equal. In some embodiments, a user of the system 100 (e.g., a doctor) may set the information related to the treatment plan before the treatment. For example, the user of the system 100 (e.g., a doctor) may set the total time of the treatment as 10 seconds, the total radiation dose during the total time of the treatment as 25 monitor units (MU), the number of control time points as 51, and the interval between each two neighboring control time points as 200 milliseconds (ms). The user of the system 100 (e.g., a doctor) may set the cumulative radiation doses associated with the control time points as {0, 0.5, 1, 1.5, 2, 4, 6, 8, 8.5, 9, 13, 15, 16, 16.5, 17, 18, 19, 19.25, 19.5, 20, . . . , 20.25, 22.5, and 25}, wherein a cumulative radiation dose may correspond to a control time point. For example, a cumulative radiation dose of 1.5 in the brackets may correspond to the fourth control time point. As another example, a cumulative radiation dose of 0 in the brackets may correspond to the first control time point (e.g., the start time of the treatment). As still another example, a cumulative radiation dose of 25 in the brackets may correspond to the last control time point (e.g., the end time of the treatment). In some embodiments, the user may set the information related to the treatment plan through the server 140 (e.g., the I/O 230) and/or the terminal 130 (e.g., the I/O 350). In some embodiments, the information related to the treatment plan may be stored in the storage device 150 and/or the storage device (e.g., the storage 220 of the server 140, the storage 390 of the terminal 130, the memory 360 of the terminal 130, etc.) The plan obtaining module 410 may obtain the information related to the treatment plan by accessing the storage device 150 and/or the storage device.

In 520, the backward window determination module 420 may determine a backward window. The backward window may refer to a time window prior to the current treatment stage. In some embodiments, the backward window determination module 420 may determine the backward window automatically. For example, the backward window determination module 420 may determine the current time as an end time of the backward window and determine a time point prior to the end time as a start time of the backward window automatically. The backward window determination module 420 may determine the backward window based on the start time and the end time. In some embodiments, the backward window determination module 420 may determine the backward window based on instructions from the user. For example, the user may input an end time (e.g., the current time) and a start time prior to the end time through the server 140 (e.g., the I/O 230) and/or the terminal 130 (e.g., the I/O 350) and send instructions related to the start time and the end time to the backward window determination module 420. After receiving the instructions, the backward window determination module 420 may determine the backward window based on the start time and the end time. In some embodiments, the closer the backward end time is to the current time, the more accurate the modulation of the one more pulse parameters of the forward window may be.

In 530, the backward information determination module 430 may determine backward information associated with the backward window. The backward information may include the actual recorded information relating to pulses that have been delivered in the backward window. The backward information determination module 430 may determine the backward information associated with the backward window based on the information related to the treatment plan, physical measurements, inferences from physical measurements, and the backward window. In some embodiments, when the radiation device 110 delivers the pluses during the treatment, the radiation device 110, the server 140 or the terminal 130 may record the delivery times at which the pulses are delivered, the cumulative radiation dose that have been delivered, and the number of pulses that have been delivered. The backward cumulative radiation dose of the backward start time may be the recorded radiation dose delivered in response to one or more pulses that have been delivered during a time period from the start time of the treatment (or treatment beam or segment) to the backward start time. The backward cumulative radiation dose of the backward end time may be the recorded radiation dose delivered in response to one or more pulses that have been delivered during a time period from the start time of the treatment (or treatment beam or segment) to the backward end time. The backward information determination module 430 may determine the backward total radiation dose by determining a difference between the cumulative radiation dose of the backward start time and the cumulative radiation dose of the backward end time. The backward information determination module 430 may determine the backward number of pulses by determining a difference between the recorded number of pulses that have been delivered during the time period from the start time of the treatment to the backward start time and the recorded number of pulses that have been delivered during the time period from the start time of the treatment to the backward end time. The backward information determination module 430 may determine the backward radiation output per pulse by dividing the backward total radiation dose by the backward number of pulses. The backward information determination module 430 may determine the radiation output rate of the backward window by dividing the radiation dose delivered in response to one or more pulses in the backward window excluding the radiation dose delivered in response to the first pulse by the backward interval.

In some embodiments, the backward interval of the backward window determined by the backward window determination module 420 may be less than or equal to a time threshold (e.g., 500 ms). Alternatively or additionally, the backward number of pulses of the backward window determined by the backward window determination module 420 may be less than or equal to a number threshold (e.g., 6). The time threshold and/or the number threshold may be a fixed value, or adjustable based on different treatments.

In all of the above aspects of the invention, it shall be clear that analysis of the backward window, or backward windows recorded during delivery of previous treatment fraction, may be used to predict the forward window and thresholds used to modulate the pulse parameter.

In 540, the forward window determination module 440 may determine a forward window based on the information related to the treatment plan. The forward window may refer to a time window after the current treatment stage. In some embodiments, the forward window determination module 440 may determine the forward window automatically. For example, the forward window determination module 440 may determine the current time as a start time of a forward window and a time point after the current time as an end time of the forward window automatically. The forward window determination module 440 may determine the forward window based on the start time and the end time. In some embodiments, the forward window determination module 440 may determine the forward window based on instructions from the user. For example, the user may input a start time (e.g., the current time) and an end time after the current time through the server 140 (e.g., the I/O 230) and/or the terminal 130 (e.g., the I/O 350) and send instructions related to the start time and the end time to the forward window determination module 440. After receiving the instructions, the forward window determination module 440 may determine the forward window based on the start time and the end time.

In 550, the forward information determination module 450 may determine forward information associated with the forward window based on the information related to the treatment plan and the backward information (including physical measurements). The forward information may include predicted or planned information relating to the pulses that are to be transmitted in the forward window. The forward information determination module 450 may use the actual measurements (e.g., the backward information) associated with the pulses that have been delivered in the backward window to predict the forward information associated with the pulses that are to be delivered in the forward window. The forward information may include a forward start time of the forward window, a forward end time of the forward window, a forward interval of the forward window, a forward cumulative radiation dose of the forward window, a forward total radiation dose of the forward window, a forward number of pulses in the forward window, or the like, or any combination thereof. The forward total radiation dose may refer to a radiation dose delivered in response to the plurality of pulses during the forward interval of the forward window. The forward cumulative radiation dose may refer to a radiation dose delivered in response to the plurality of pulses from the start time of the treatment to the forward end time. The forward number of pulses may refer to the number of pulses delivered during the forward interval.

The forward information determination module 450 may determine the forward interval of the forward window based on the information related to the treatment plan. In some embodiments, the first forward interval may be equal to the interval between each two neighboring control time points in the forward window (e.g., 200 ms).

The forward information determination module 450 may determine the forward cumulative radiation dose based on the information related to the treatment plan. The forward cumulative radiation dose may refer to a cumulative radiation dose associated with a forward end time of the forward window. The forward cumulative radiation dose may refer to a radiation dose delivered in response to one or more pulses from the start time of the treatment to the forward end time of the forward window. In some embodiments, there may be a relationship between a time point within the total time of the treatment and a cumulative radiation dose associated with the time point. In some embodiments, the server 140 may determine the relationship based on the cumulative radiation doses associated with the control time points related to the treatment plan. In some embodiments, the server 140 may determine the relationship by fitting a continuity equation or a discrete equation. In some embodiments, the fitting method may include interpolation, extrapolation, smoothing, regression analysis, the least square method, or the like, or any combination thereof. Exemplary interpolation methods may include Lagrange interpolation, Newton interpolation, Hermite interpolation, piecewise interpolation, spline interpolation, linear interpolation, or the like, or a combination thereof. Exemplary extrapolation methods may include linear extrapolation, polynomial extrapolation, conic extrapolation, French curve extrapolation, linear predictors, Kalman filtering, extended Kalman filtering, neural-network predictors, or the like, or a combination thereof. Exemplary regression analysis may include linear regression, nonlinear regression, multiple regression, logistic regression, partial regression, or the like, or a combination thereof. With the determined relationship (e.g., a planned cumulative radiation function), the server 140 may determine a cumulative radiation dose associated with any time point within the total time of the treatment.

The forward information determination module 450 may determine the forward radiation dose based on the forward cumulative radiation dose. In some embodiments, the forward information determination module 450 may determine the forward radiation dose by subtracting a cumulative radiation dose associated with the forward start time (e.g., the current time) from a cumulative radiation dose associated with the forward end time (e.g., the forward cumulative radiation dose). In a condition that the forward start time is equal to the current time, the forward information determination module 450 may determine the cumulative radiation dose of the current time (e.g., an actually recorded radiation dose delivered in response to one or more pulses that have been transmitted during a time period from the start time of the treatment to the current time) as the cumulative radiation dose associated with the forward start time. For example, if both of the forward start time and the backward end time are equal to the current time, the forward information determination module 450 may determine the backward cumulative radiation dose as the cumulative radiation dose associated with the forward start time. In a condition that the forward start time is behind the current time, the forward information determination module 450 may determine the cumulative radiation dose associated with the forward start time based on the planned cumulative radiation function.

The forward information determination module 450 may determine the forward number of pulses in the forward window based on a backward radiation output per pulse (e.g., as described in connection with step 530 in FIG. 5 above) and the forward radiation dose. In some embodiments, the forward information determination module 450 may determine the forward number of pulses in the forward window by dividing the forward radiation dose by the backward radiation output per pulse. In a condition that the forward window is the first forward window in the treatment (e.g., the forward start time is equal to the start time of the treatment), the forward information determination module 450 may determine the forward number of pulses in the forward window by dividing the forward radiation dose by the radiation output per pulse related to the treatment plan.

In 560, the pulse parameter determination module 460 may determine one or more pulse parameter of the forward window based on the forward information. The one or more pulse parameters of the forward window may include at least one of pulse energy, a pulse period, a pulse duty cycle, a pulse shape, or a pulse amplitude. The pulse period of the forward window may refer to an interval between each two neighboring pulses delivered in the forward window. In some embodiments, the pulse parameter determination module 460 may determine the pulse period of the forward window based on the forward interval and the forward number of pulses. Further, the pulse parameter determination module 460 may determine the pulse period of the forward window by dividing the forward interval by the forward number of pulses.

The pulse parameter determination module 460 may determine whether the pulse period is less than a time threshold. The time threshold may be a minimum interval between each two neighboring pulses delivered in the forward window allowed by the system 100 (e.g., 2.5 ms). The time threshold may be a fixed value, or adjustable based on different treatments.

The pulse parameter determination module 460 may determine a modified pulse period of the forward window based on the time threshold in response to the determination that the pulse period is less than the time threshold. In some embodiments, the pulse parameter determination module 460 may determine a pulse period that is greater than or equal to the time threshold as the modified pulse period. For example, the pulse parameter determination module 460 may determine the time threshold as the modified pulse period.

In some embodiments, after the server 140 and/or the terminal 130 determines the one or more pulse parameters of the forward window, the radiation device 110 may deliver pulses based on the one or more pulse parameters in the forward window.

In 570, the pulse parameter determination module 460 may determine whether the total radiation dose related to the treatment plan has been completed. The server 140 and/or the terminal 130 may repeat steps 520-560 to determine one or more pulse parameters in a next forward window in response to the determination that the total radiation dose related to the treatment plan has not been completed. The server 140 may terminate the process/method 500 in response to the determination that the total radiation dose related to the treatment plan has been completed. In some embodiments, a forward window in the treatment may be arranged subsequent to another forward window. For example, the end time of a first forward window may be set as the start time of a second forward window. Alternatively, there may be an interval between the end time of a forward window and the start time of another forward window next to the forward window.

Figure 6:
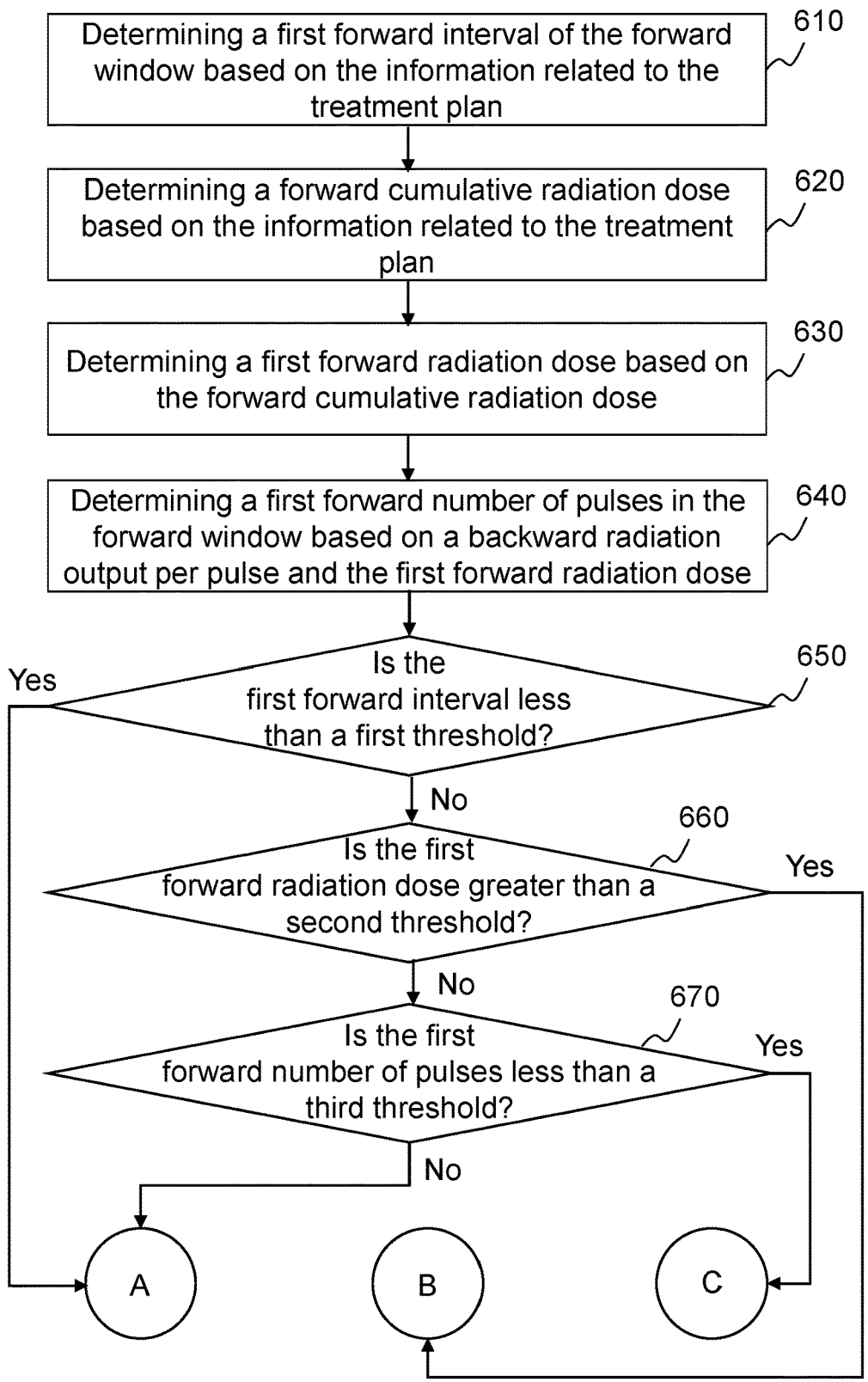
FIG. 6 is a flowchart illustrating an exemplary process for determining forward information associated with the forward window according to some embodiments of the present disclosure.

FIG. 6 is a flowchart illustrating an exemplary process/method 600 for determining forward information associated with the forward window according to some embodiments of the present disclosure. In some embodiments, the process/method 600 may be implemented in the system 100 illustrated in FIG. 1. For example, the process/method 600 may be stored in the storage device 150 and/or a storage device (e.g., the storage 220 of the server 140, the storage 390 of the terminal 130, the memory 360, etc.) as a form of instructions, and invoked and/or executed by the server 140 (e.g., the processor 210 of the server 140, or one or more modules in the server 140 illustrated in FIG. 4) and/or the terminal 130 (e.g., the CUP 340 of the terminal 130, or the GPU 330 of the terminal 130). The operations of the illustrated process/method presented below are intended to be illustrative. In some embodiments, the process/method 600 may be accomplished with one or more additional operations not described, and/or without one or more of the operations discussed. Additionally, the order in which the operations of the process/method 600 as illustrated in FIG. 6 and described below is not intended to be limiting. In some embodiments, step 550 illustrated in FIG. 5 may be performed according to the process/method 600.

In 610, the forward information determination module 450 may determine a first forward interval of the forward window based on the information related to the treatment plan. In some embodiments, the first forward interval may be equal to the interval between each two neighboring control time points in the forward window (e.g., 200 ms).

In 620, the forward information determination module 450 may determine a forward cumulative radiation dose based on the information related to the treatment plan. The forward cumulative radiation dose may refer to a cumulative radiation dose associated with a forward end time of the forward window. The forward cumulative radiation dose may refer to a radiation dose delivered in response to one or more pulses from the start time of the treatment to the forward end time of the forward window. In some embodiments, there may be a relationship between a time point within the total time of the treatment and a cumulative radiation dose associated with the time point. In some embodiments, the server 140 may determine the relationship based on the cumulative radiation doses associated with the control time points related to the treatment plan. In some embodiments, the server 140 may determine the relationship by fitting a continuity equation or a discrete equation. In some embodiments, the fitting method may include interpolation, extrapolation, smoothing, regression analysis, the least square method, or the like, or any combination thereof. Exemplary interpolation methods may include Lagrange interpolation, Newton interpolation, Hermite interpolation, piecewise interpolation, spline interpolation, linear interpolation, or the like, or a combination thereof. Exemplary extrapolation methods may include linear extrapolation, polynomial extrapolation, conic extrapolation, French curve extrapolation, or the like, linear predictors, Kalman filtering, extended Kalman filtering, neural-network predictors, or a combination thereof. Exemplary regression analysis may include linear regression, nonlinear regression, multiple regression, logistic regression, partial regression, or the like, or a combination thereof. With the determined relationship (e.g., a planned cumulative radiation function), the server 140 may determine a cumulative radiation dose associated with any time point within the total time of the treatment.

In 630, the forward information determination module 450 may determine a first forward radiation dose based on the forward cumulative radiation dose. In some embodiments, the forward information determination module 450 may determine the first forward radiation dose by subtracting a cumulative radiation dose associated with the forward start time (e.g., the current time) from a cumulative radiation dose associated with the forward end time (e.g., the forward cumulative radiation dose). In a condition that the forward start time is equal to the current time, the forward information determination module 450 may determine the cumulative radiation dose of the current time (e.g., an actually recorded radiation dose delivered in response to one or more pulses that have been transmitted during a time period from the start time of the treatment to the current time) as the cumulative radiation dose associated with the forward start time. For example, if both of the forward start time and the backward end time are equal to the current time, the forward information determination module 450 may determine the backward cumulative radiation dose as the cumulative radiation dose associated with the forward start time. In a condition that the forward start time is behind the current time, the forward information determination module 450 may determine the cumulative radiation dose associated with the forward start time based on the planned cumulative radiation function.

In 640, the forward information determination module 450 may determine a first forward number of pulses in the forward window based on a backward radiation output per pulse (e.g., as described in connection with step 530 in FIG. 5 above) and the first forward radiation dose. In some embodiments, the forward information determination module 450 may determine the first forward number of pulses in the forward window by dividing the first forward radiation dose by the backward radiation output per pulse. In a condition that the forward window is the first forward window in the treatment, the forward information determination module 450 may determine the first forward number of pulses in the forward window by dividing the first forward radiation dose by the radiation output per pulse related to the treatment plan.

In 650, the forward information determination module 450 may determine whether the first forward interval is less than a first threshold. In some embodiments, the first threshold may be equal to the interval between each two neighboring control time points in the forward window (e.g., 200 ms). The process/method 600 may proceed to 660 in response to the determination that the first forward interval is greater than or equal to the first threshold. The process/method 600 may proceed to mode A in which the forward information determination module 450 may perform no modification on the first forward interval, the first forward radiation dose, and the first forward number of pulses in response to the determination that the first forward interval is less than the first threshold. For example, the forward window determination module 440 may determine a forward window with a fixed forward interval in each iteration (e.g., from steps 520-570). The fixed forward interval may be equal to the interval between each two neighboring control time points (e.g., 200 ms). When the treatment proceeds to a stage close to the end of the treatment (e.g., the interval between the current time and the end time of the treatment is less than the interval between each two neighboring control time points), the forward window determination module 440 may determine a forward window with a forward interval less than the interval between each two neighboring control time points. In this condition, the process/method 600 may proceed to mode A in which the forward information determination module 450 may perform no modification on the first forward interval, the first forward radiation dose, and the first forward number of pulses in response to the determination that the first forward interval is less than the first threshold (e.g., the interval between each two neighboring control time points).

In 660, the forward information determination module 450 may determine whether the first forward radiation dose is greater than a second threshold. In some embodiments, the second threshold may be a maximum radiation dose for each forward window in a treatment (e.g., 0.25 MU) allowed by the system 100. The second threshold may be a fixed value, or adjustable based on different treatments. The process/method 600 may proceed to 670 in response to the determination that the first forward radiation dose is less than or equal to the second threshold. The process/method 600 may proceed to mode B to modify the first forward radiation dose, the first forward interval, and the first forward number of pulses dose based on the second threshold (e.g., as will be descried in detail in connection with FIG. 7) in response to the determination that the first forward radiation dose is greater than the second threshold, which indicates that there are more forward radiation dose than the maximum radiation dose allowed by the system 100 in the forward window.

In 670, the forward information determination module 450 may determine whether the first forward number of pulses is less than a third threshold. In some embodiments, the third threshold may be a minimum number of pulses for each forward window in a treatment (e.g., 6 pulses) allowed by the system 100. The third threshold may be a fixed value, or adjustable based on different treatments. The process/method 600 may proceed to mode C to modify the first forward radiation dose, the first forward interval, and the first forward number of pulses dose based on the third threshold (e.g., as will be descried in detail in connection with FIG. 8) in response to the determination that the first forward number of pulses is less than the third threshold, which indicates that there are not enough pulses in the forward window. The process/method 600 may proceed to mode A in which the forward information determination module 450 may perform no modification on the first forward interval, the first forward radiation dose, and the first forward number of pulses in response to the determination that the first forward number of pulses is greater than or equal to the third threshold, which indicates that the forward radiation dose in the forward window is not more than the maximum radiation dose allowed by the system 100 and there are enough pluses in the forward window.

Figure 7:
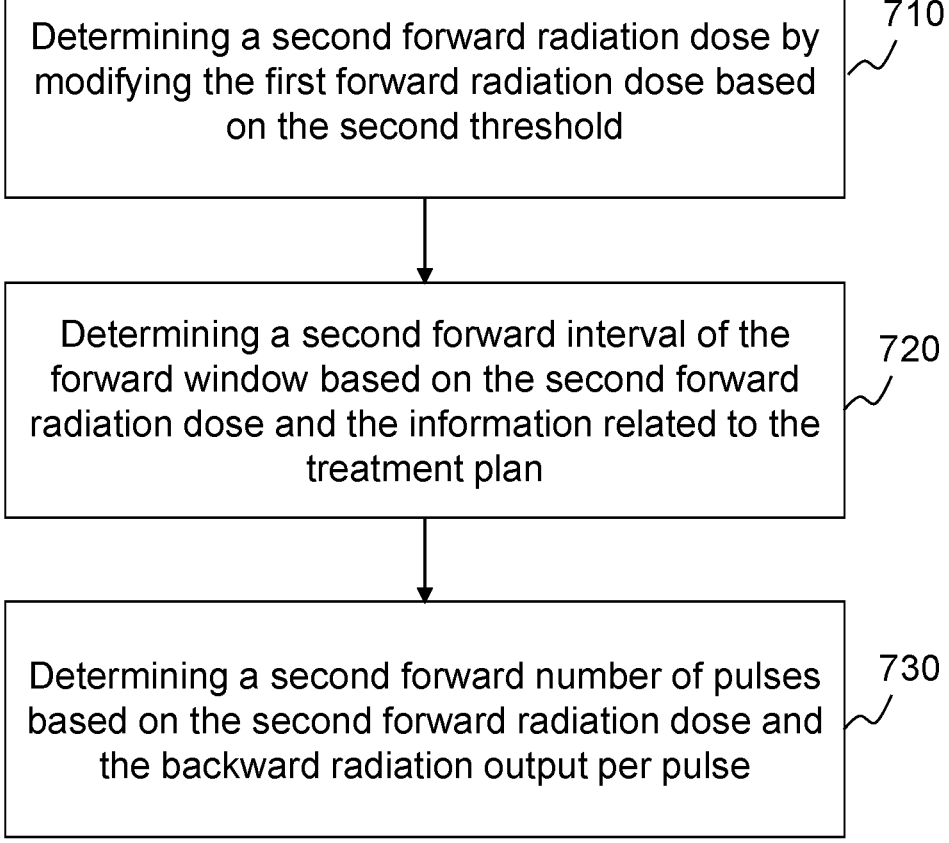
FIG. 7 is a flowchart illustrating an exemplary process for determining a second forward number of pulses and a second forward interval according to some embodiments of the present disclosure.

FIG. 7 is a flowchart illustrating an exemplary process/method 700 for determining a second forward number of pulses and a second forward interval according to some embodiments of the present disclosure. In some embodiments, the process/method 700 may be implemented in the system 100 illustrated in FIG. 1. For example, the process/method 700 may be stored in the storage device 150 and/or a storage device (e.g., the storage 220 of the server 140, the storage 390 of the terminal 130, the memory 360 of the terminal 130, etc.) as a form of instructions, and invoked and/or executed by the server 140 (e.g., the processor 210 of the server 140, or one or more modules in the server 140 illustrated in FIG. 4) and/or the terminal 130 (e.g., the CUP 340 of the terminal 130, or the GPU 330 of the terminal 130). The operations of the illustrated process/method presented below are intended to be illustrative. In some embodiments, the process/method 700 may be accomplished with one or more additional operations not described, and/or without one or more of the operations discussed. Additionally, the order in which the operations of the process/method 700 as illustrated in FIG. 7 and described below is not intended to be limiting. In some embodiments, mode B illustrated in FIG. 6 may be performed according to the process/method 700 to modify the first forward radiation dose, the first forward interval, and the first forward number of pulses dose based on the second threshold (e.g., the maximum radiation dose for each forward window in a treatment allowed by the system 100).

In 710, the forward information determination module 450 may determine a second forward radiation dose by modifying the first forward radiation dose based on the second threshold. In some embodiments, the forward information determination module 450 may determine a radiation dose that is less than or equal to the second threshold as the second forward radiation dose. For example, the forward information determination module 450 may determine the second threshold as the second forward radiation dose.

In 720, the forward information determination module 450 may determine a second forward interval of the forward window based on the second forward radiation dose and the information related to the treatment plan. In some embodiments, the forward information determination module 450 may determine the second forward interval by modifying the first forward interval to match the second forward radiation dose. In some embodiments, the forward information determination module 450 may determine the forward cumulative radiation dose based on the second forward radiation dose, and determine the second forward interval based on the forward cumulative radiation dose and the planned cumulative radiation function.

The forward information determination module 450 may determine the forward cumulative radiation dose by adding a cumulative radiation dose associated with the forward start time (e.g., the current time) to the second forward radiation dose. In a condition that the forward start time is equal to the current time, the forward information determination module 450 may determine the cumulative radiation dose of the current time (e.g., an actually recorded radiation dose delivered in response to one or more pulses that have been transmitted during a time period from the start time of the treatment to the current time) as the cumulative radiation dose associated with the forward start time. For example, if both of the forward start time and the backward end time are equal to the current time, the forward information determination module 450 may determine the backward cumulative radiation dose as the cumulative radiation dose associated with the forward start time. In a condition that the forward start time is behind the current time, the forward information determination module 450 may determine the cumulative radiation dose associated with the forward start time based on the planned cumulative radiation function. The forward information determination module 450 may determine the time point corresponding to the forward cumulative radiation dose based on the planned cumulative radiation function, and determine the second forward interval by subtracting the forward start time from the time point corresponding to the forward cumulative radiation dose.

In 730, the forward information determination module 450 may determine a second forward number of pulses based on the second forward radiation dose and the backward radiation output per pulse. In some embodiments, the forward information determination module 450 may determine the second forward number of pulses in the forward window by dividing the second forward radiation dose by the backward radiation output per pulse (e.g., as described in connection with step 530 in FIG. 5 above). In a condition that the forward window is the first forward window in the treatment, the forward information determination module 450 may determine the second forward number of pulses in the forward window by dividing the second forward radiation dose by the radiation output per pulse related to the treatment plan.

In some embodiments, the forward information determination module 450 may perform step 720 before or after step 730. In some embodiments, the forward information determination module 450 may perform step 720 and step 730 simultaneously.

Figure 8:
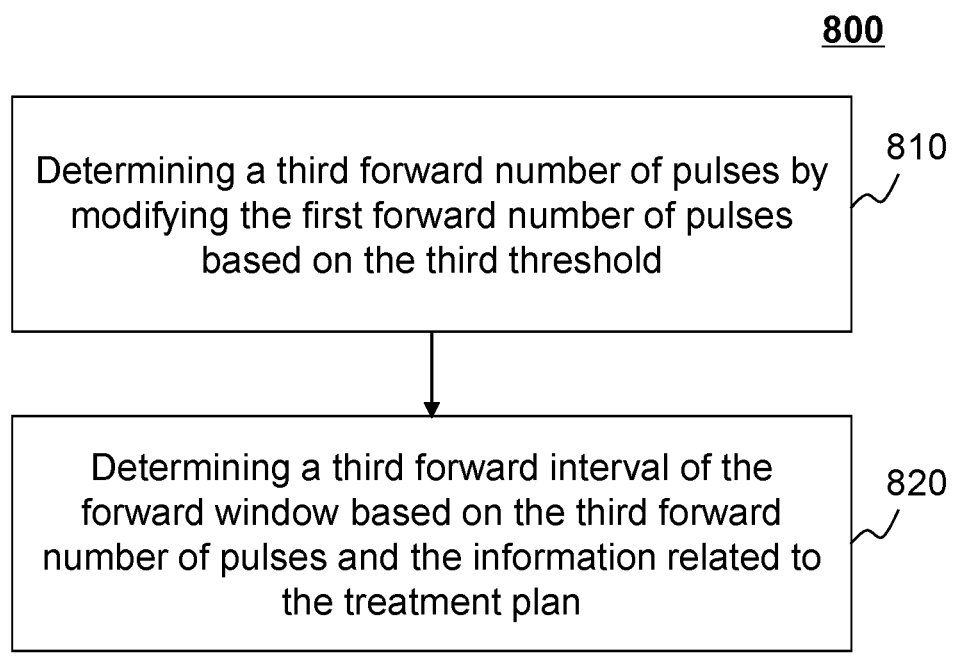
FIG. 8 is a flowchart illustrating an exemplary process for determining a third forward number of pulses and a third forward interval according to some embodiments of the present disclosure.

FIG. 8 is a flowchart illustrating an exemplary process/method 800 for determining a third forward interval and a third forward number of pulses according to some embodiments of the present disclosure. In some embodiments, the process/method 800 may be implemented in the system 100 illustrated in FIG. 1. For example, the process/method 800 may be stored in the storage device 150 and/or a storage device (e.g., the storage 220 of the server 140, the storage 390 of the terminal 130, the memory 360 of the terminal 130, etc.) as a form of instructions, and invoked and/or executed by the server 140 (e.g., the processor 210 of the server 140, or one or more modules in the server 140 illustrated in FIG. 4) and/or the terminal 130 (e.g., the CUP 340 of the terminal 130, or the GPU 330 of the terminal 130). The operations of the illustrated process/method presented below are intended to be illustrative. In some embodiments, the process/method 800 may be accomplished with one or more additional operations not described, and/or without one or more of the operations discussed. Additionally, the order in which the operations of the process/method 800 as illustrated in FIG. 8 and described below is not intended to be limiting. In some embodiments, mode C illustrated in FIG. 6 may be performed according to the process/method 800 to modify the first forward radiation dose, the first forward interval, and the first forward number of pulses dose based on the third threshold (e.g., the minimum number of pulses for each forward window in a treatment allowed by the system 100).

In 810, the forward information determination module 450 may determine a third forward number of pulses by modifying the first forward number of pulses based on the third threshold. In some embodiments, the forward information determination module 450 may determine a number that is greater than or equal to the third threshold as the third forward number of pulses. For example, the forward information determination module 450 may determine the third threshold as the third forward number of pulses.

In 820, the forward information determination module 450 may determine a third forward interval of the forward window based on the third forward number of pulses and the information related to the treatment plan. In some embodiments, the forward information determination module 450 may determine the third forward interval by modifying the first forward interval to match the third forward number of pulses. In some embodiments, the forward information determination module 450 may determine the forward radiation dose based on the third forward number of pulses, determine the forward cumulative radiation dose based on the forward radiation dose, and determine the third forward interval based on the forward cumulative radiation dose and the planned cumulative radiation function. In some embodiments, the forward information determination module 450 may determine the forward radiation dose by multiplying the third forward number of pulses by the backward radiation output per pulse (e.g., as described in connection with step 530 in FIG. 5 above). In a condition that the forward window is the first forward window of the treatment, the forward information determination module 450 may determine the forward radiation dose by multiplying the third forward number of pulses by the radiation output per pulse related to the treatment plan.

The forward information determination module 450 may determine the forward cumulative radiation dose by adding a cumulative radiation dose associated with the forward start time (e.g., the current time) to the forward radiation dose. In a condition that the forward start time is equal to the current time, the forward information determination module 450 may determine the cumulative radiation dose of the current time (e.g., an actually recorded radiation dose delivered in response to one or more pulses that have been transmitted during a time period from the start time of the treatment to the current time) as the cumulative radiation dose associated with the forward start time. For example, if both of the forward start time and the backward end time are equal to the current time, the forward information determination module 450 may determine the backward cumulative radiation dose as the cumulative radiation dose associated with the forward start time. In a condition that the forward start time is behind the current time, the forward information determination module 450 may determine the cumulative radiation dose associated with the forward start time based on the planned cumulative radiation function. The forward information determination module 450 may determine the time point corresponding to the forward cumulative radiation dose based on the planned cumulative radiation function, and determine the third forward interval by subtracting the forward start time from the time point corresponding to the forward cumulative radiation dose.

Figure 9:
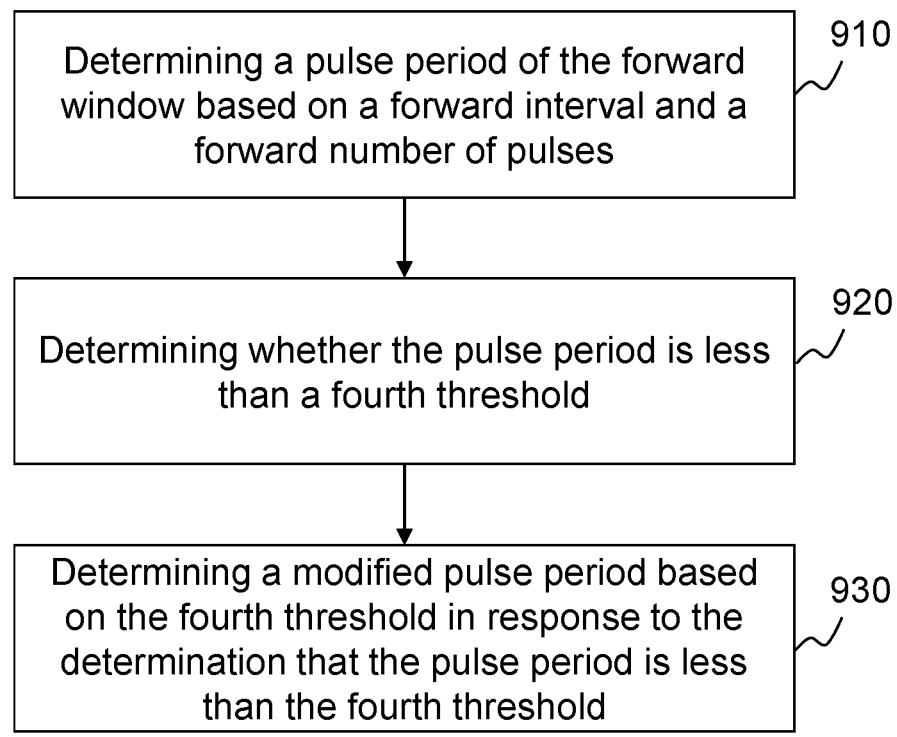
FIG. 9 is a flowchart illustrating an exemplary process for determining a pulse period of a forward window according to some embodiments of the present disclosure.

FIG. 9 is a flowchart illustrating an exemplary process for determining a pulse period of the forward window according to some embodiments of the present disclosure. In some embodiments, the process/method 900 may be implemented in the system 100 illustrated in FIG. 1. For example, the process/method 900 may be stored in the storage device 150 and/or a storage device (e.g., the storage 220 of the server 140, the storage 390 of the terminal 130, the memory 360 of the terminal 130, etc.) as a form of instructions, and invoked and/or executed by the server 140 (e.g., the processor 210 of the server 140, or one or more modules in the server 140 illustrated in FIG. 4) and/or the terminal 130 (e.g., the CUP 340 of the terminal 130, or the GPU 330 of the terminal 130). The operations of the illustrated process/method presented below are intended to be illustrative. In some embodiments, the process/method 900 may be accomplished with one or more additional operations not described, and/or without one or more of the operations discussed. Additionally, the order in which the operations of the process/method 900 as illustrated in FIG. 9 and described below is not intended to be limiting. In some embodiments, step 560 illustrated in FIG. 5 may be performed according to the process/method 900.

In 910, the pulse parameter determination module 460 may determine a pulse period of the forward window based on a forward interval and a forward number of pulses. The pulse period of the forward window may refer to an interval between each two neighboring pulses delivered in the forward window. In some embodiments, the pulse parameter determination module 460 may determine the pulse period of the forward window by dividing the forward interval by the forward number of pulses. In some embodiments, the pulse parameter determination module 460 may determine the pulse period of the forward window based on the first forward interval and the first forward number of pulses in response to mode A. In some embodiments, the pulse parameter determination module 460 may determine the pulse period of the forward window based on the second forward interval and the second forward number of pulses in response to mode B. In some embodiments, the pulse parameter determination module 460 may determine the pulse period of the forward window based on the third forward interval and the third forward number of pulses in response to mode C.

In 920, the pulse parameter determination module 460 may determine whether the pulse period is less than a fourth threshold. The fourth threshold may be a minimum interval between each two neighboring pulses delivered in the forward window allowed by the system 100 (e.g., 2.5 ms). The fourth threshold may be a fixed value, or adjustable based on different treatments.

In 930, the pulse parameter determination module 460 may determine a modified pulse period of the forward window based on the fourth threshold in response to the determination that the pulse period is less than the fourth threshold. In some embodiments, the pulse parameter determination module 460 may determine a pulse period that is greater than or equal to the fourth threshold as the modified pulse period. For example, the pulse parameter determination module 460 may determine the fourth threshold as the modified pulse period.

After the server 140 determines the pulse period of the forward window, the radiation device 110 may delivery radiation pulses in the forward window based on the pulse period.

In this disclosure, the server 140 may modulate the pulse period by modulating the forward interval and the forward number of pulses. Similarly, the server 140 may modulate pulse energy, a pulse duty cycle, a pulse shape, or a pulse amplitude in a way similar to the description in the disclosure. In some embodiments, the server 140 may modulate the pulse energy, the pulse duty cycle, the pulse shape, or the pulse amplitude, in conjunction with the pulse period.

FIGS. 10-14 illustrate results of modulating the period pulse using systems and methods for pulse parameter modulation described in the disclosure.

Figure 10:
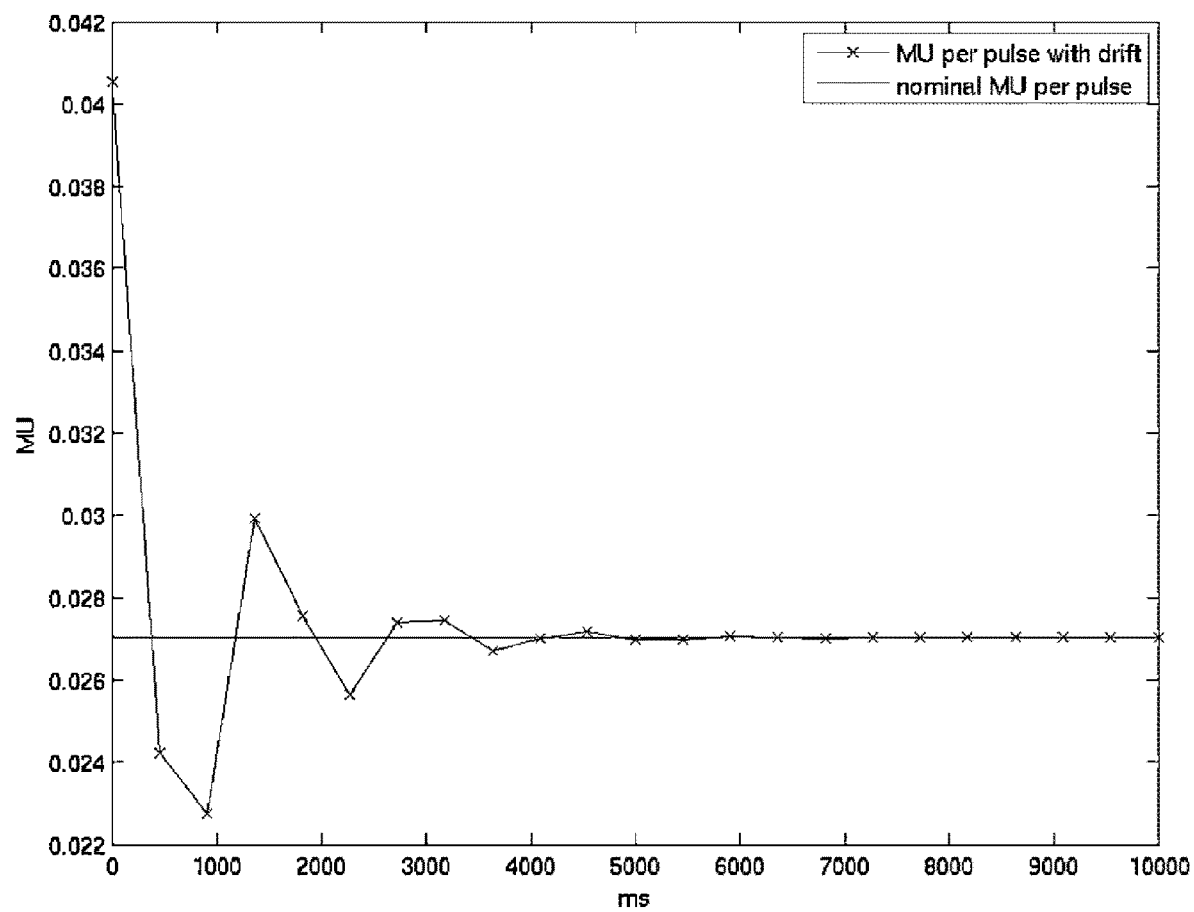
FIG. 10 illustrates an example of radiation output per pulse arbitrary drift function used in simulation to test robustness against drift over the course of a treatment according to some embodiments of the present disclosure.

FIG. 10 illustrates an example of radiation output per pulse arbitrary drift function used in simulation to test robustness against drift over the course of a treatment according to some embodiments of the present disclosure. As shown in FIG. 10, the X axis represents the delivery time. The unit of the delivery time is millisecond (ms). The Y axis represents the radiation output per pulse. The unit of the radiation output per pulse is monitor unit (MU). The line without dots represents a nominal radiation output per pulse of 0.027 MU during the treatment (e.g., from 0 ms to 10000 ms). The dotted line represents an actual radiation output per pulse during the treatment (e.g., from 0 ms to 10000 ms). As shown in FIG. 10, the actual radiation output per pulse was stable and close to the nominal radiation output per pulse from about 4000 ms.

Figure 11:
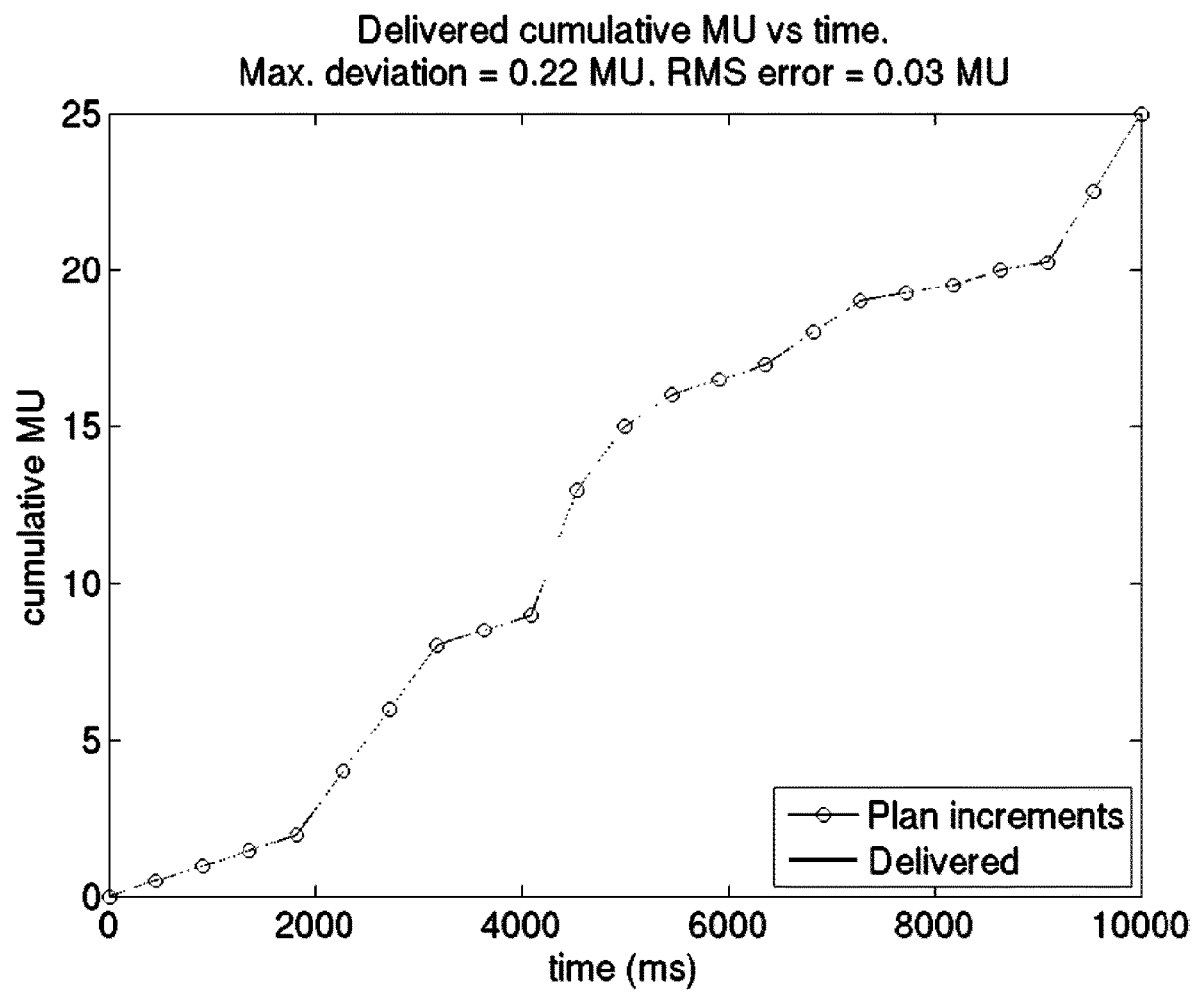
FIG. 11 illustrates an example of a comparison result of planned cumulative radiation doses and actual cumulative radiation doses according to some embodiments of the present disclosure, when the MU per pulse varies as shown in FIG. 10, with the addition of stochastic noise.

FIG. 11 illustrates an example of a comparison result of planned cumulative radiation doses and actual cumulative radiation doses according to some embodiments of the present disclosure. As shown in FIG. 11, the X axis represents the delivery time. The unit of the delivery time is millisecond (ms). The Y axis represents the cumulative radiation dose. The unit of the radiation output per pulse is monitor unit (MU). The line without circles represents the actual cumulative radiation doses during the treatment (e.g., from 0 ms to 10000 ms). The line with circles represents the planned cumulative radiation doses during the treatment (e.g., from 0 ms to 10000 ms). As shown in FIG. 11, the actual cumulative radiation doses were basically consistent with the planned cumulative radiation doses. The maximum deviation between the planned cumulative radiation doses and the actual cumulative radiation doses was 0.22 MU. The root mean square (RMS) error was 0.03 MU. This consistency is observed notwithstanding the presence of additive stochastic noise to the MU per pulse, as well as the systematic variation shown in FIG. 10.

Figure 12:
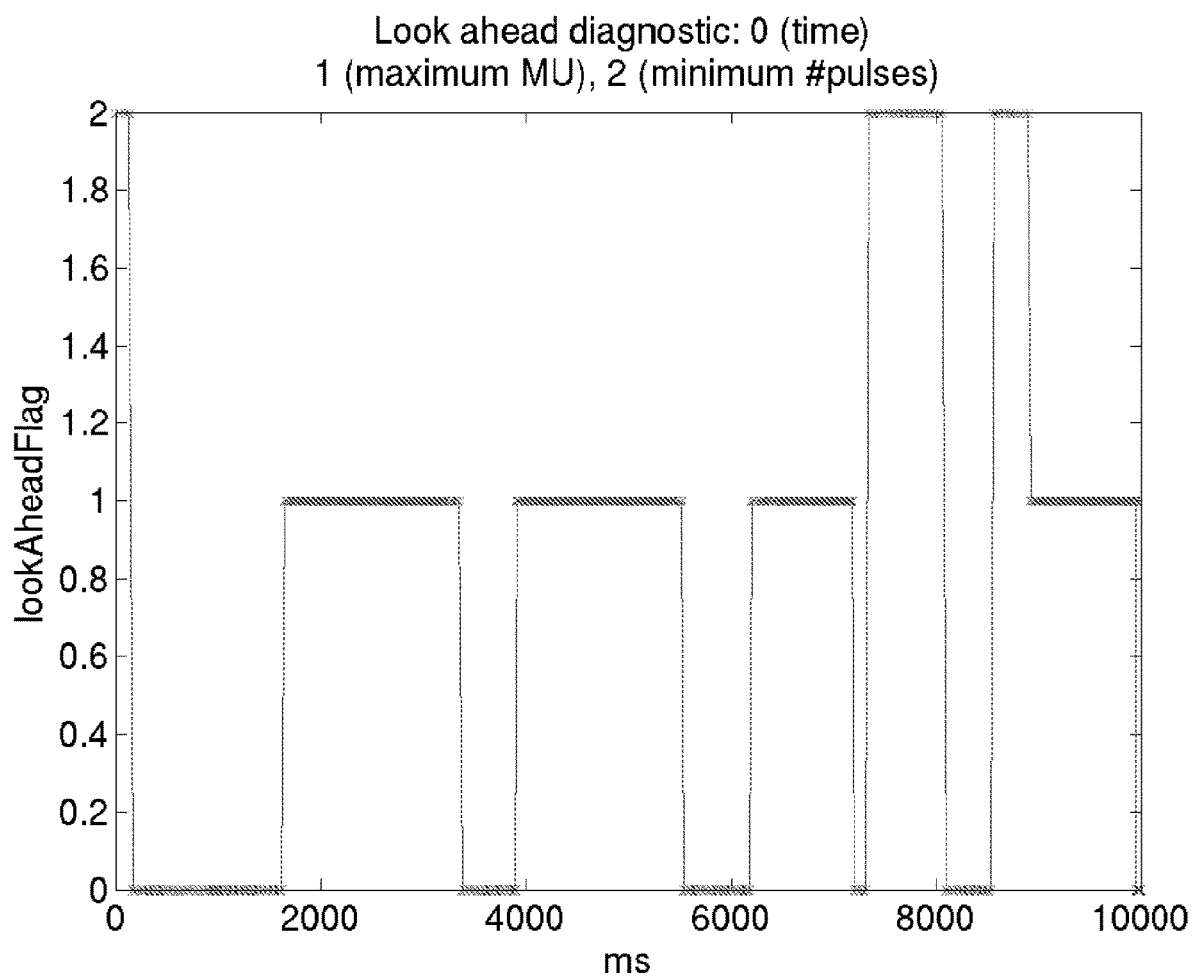
FIG. 12 illustrates an example of mode A, mode B, and mode C used in the pulse parameter modulation in a treatment according to some embodiments of the present disclosure, when the MU per pulse varies as shown in FIG. 10, with the addition of stochastic noise.

FIG. 12 illustrates an example of mode A, mode B, and mode C used in the pulse parameter modulation in a treatment according to some embodiments of the present disclosure. As shown in FIG. 12, the X axis represents delivery time. The unit of the delivery time is millisecond (ms). The Y axis represents the type of mode. "0" represents mode A, "1" represents mode B, and "2" represents mode C.

Figure 13:
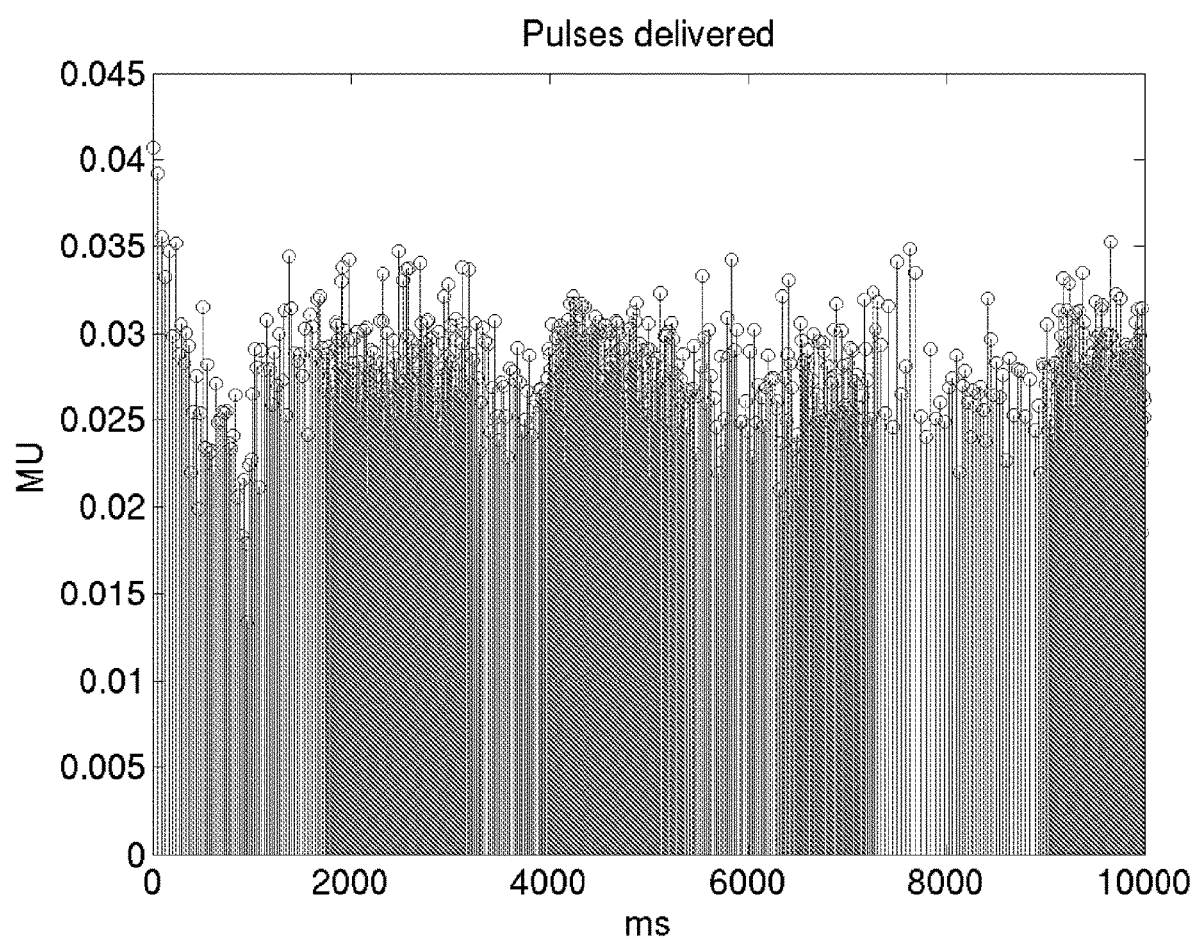
FIG. 13 illustrates an example of pulses delivered during a treatment according to some embodiments of the present disclosure, when the MU per pulse varies as shown in FIG. 10, with the addition of stochastic noise.

FIG. 13 illustrates an example of pulses delivered during a treatment according to some embodiments of the present disclosure. As shown in FIG. 13, the X axis represents the delivery time. The unit of the delivery time is millisecond (ms). The Y axis represents the radiation output per pulse. The unit of the radiation output per pulse is monitor unit (MU). Each line with a circle represents a pulse delivered in the treatment. The interval with dense pulses (e.g., 2000 ms-3000 ms) represents that the pulse period in the interval was relatively short. The interval with sparse pulses (e.g., 7500 ms-9000 ms) represents that the pulse period in the interval was relatively long.

Figure 14:
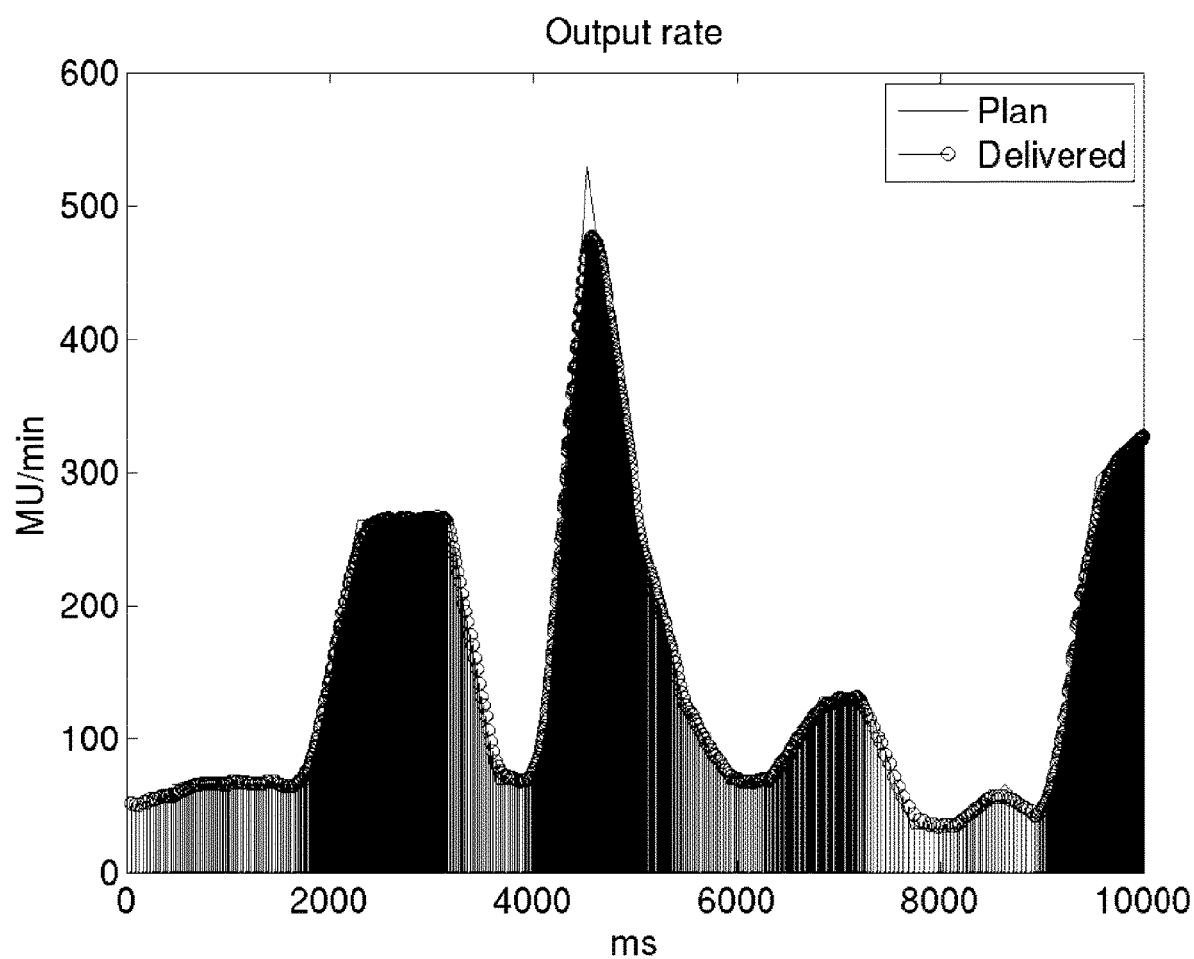
FIG. 14 illustrates an example of a comparison result of planned radiation output rates and actual radiation output rates according to some embodiments of the present disclosure, when the MU per pulse varies as shown in FIG. 10 with the addition of stochastic noise.

FIG. 14 illustrates an example of a comparison result of planned radiation output rates and actual radiation output rates according to some embodiments of the present disclosure. As shown in FIG. 14, the X axis represents delivery time. The unit of the delivery time is millisecond (ms). The Y axis represents the radiation output rate. The unit of the radiation output rate is MU/min. The line without circles represents the planned radiation output rates during the treatment (e.g., from 0 ms to 10000 ms). The line with circles represents the actual radiation output rates during the treatment (e.g., from 0 ms to 10000 ms). As shown in FIG. 11, the actual radiation output rates were basically consistent with the planned radiation output rates. This consistency is observed notwithstanding the presence of additive stochastic noise to the MU per pulse, as well as the systematic variation shown in FIG. 10.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for pulse parameter modulation, comprising:
   one or more storage media comprising a set of instructions for modulating one or more pulse parameters; and
   one or more processors configured to communicate with the one or more storage media, wherein when executing the set of instructions, the one or more processors are directed to cause the system to perform operations including:
   obtaining information related to a treatment plan;
   determining a backward window based on the information related to the treatment plan, within which one or more radiation pulses have been transmitted;
   determining backward information associated with the backward window based on the information related to the treatment plan and the backward window;
   determining, based on the information related to the treatment plan, a forward window within which one or more radiation pulses are to be transmitted;
   determining forward information associated with the forward window based on the information related to the treatment plan, the backward information, and the forward window, the forward information including at least one of a first forward interval of the forward window, a first forward radiation output of the forward window, or a first forward number of pulses of the forward window;
   modifying the forward information based on a threshold, the threshold relating to the one or more radiation pulses to be transmitted in the forward window; and
   determining one or more pulse parameters of the forward window based on the modified forward information.

2. The system of claim 1, wherein the information related to the treatment plan includes at least one of
   a total time of a treatment,
   a total radiation during the total time of the treatment,
   one or more control time points within the total time of the treatment,
   a radiation output rate associated with each of the one or more control time points within the total time of the treatment,
   a radiation output per pulse,
   a cumulative radiation associated with each of the one or more control time points within the total time of the treatment, or
   an interval between each two neighboring control time points within the total time of the treatment.

3. The system of claim 1, wherein the backward information includes at least one of
   a backward total radiation of the backward window,
   a backward cumulative radiation output of the backward window,
   a backward interval of the backward window,
   a backward number of pulses in the backward window, or
   a backward radiation output per pulse of the backward window.

4. The system of claim 3, wherein determining the forward information associated with the forward window based on the information related to the treatment plan, the backward information, and the forward window includes:
   determining the first forward interval of the forward window based on the information related to the treatment plan;

determining a forward cumulative radiation output based on the information related to the treatment plan;

determining the first forward radiation output based on the forward cumulative radiation output; and determining the first forward number of pulses in the forward window based on the backward radiation output per pulse and the first forward radiation output.

5. The system of claim 4, wherein modifying the forward information based on the threshold includes:

determining whether the first forward interval is less than a first threshold; and determining whether the first forward radiation output is greater than a second threshold in response to a determination that the first forward interval is greater than or equal to the first threshold.

6. The system of claim 5, wherein modifying the forward information based on the threshold includes:

determining a second forward radiation output by modifying the first forward radiation output based on the second threshold in response to a determination that the first forward radiation output is greater than the second threshold;

determining a second forward interval based on the second forward radiation output and the information related to the treatment plan; and determining a second forward number of pulses based on the second forward radiation output and the backward radiation output per pulse.

7. The system of claim 5, wherein modifying the forward information based on the threshold includes:

determining whether the first forward number of pulses is less than a third threshold in response to a determination that the first forward radiation output is less than or equal to the second threshold;

determining a third forward number of pulses by modifying the first forward number of pulses based on the third threshold in response to a determination that the first forward number of pulses is less than the third threshold; and determining a third forward interval based on the third forward number of pulses and the information related to the treatment plan.

8. The system of claim 1, wherein the one or more pulse parameters of the forward window includes at least one of pulse energy, a pulse period, a pulse duty cycle, a pulse shape, or a pulse amplitude.

9. The system of claim 8, wherein determining one or more pulse parameters of the forward window based on the modified forward information includes:

determining the pulse period of the forward window based on a fourth forward interval and a fourth forward number of pulses.

10. The system of claim 9, wherein determining one or more pulse parameters of the forward window based on the modified forward information includes:

determining whether the pulse period is less than a fourth threshold; and determining a modified pulse period based on the fourth threshold in response to a determination that the pulse period is less than the fourth threshold.

11. A method for pulse parameter modulation implemented on a computing device having one or more processors and one or more storage media, the method comprising:

obtaining, by the one or more processors, information related to a treatment plan;

determining, by the one or more processors, a backward window based on the information related to the treatment plan, within which one or more radiation pulses have been transmitted;

determining, by the one or more processors, backward information associated with the backward window based on the information related to the treatment plan and the backward window;

determining, by the one or more processors based on the information related to the treatment plan, a forward window within which one or more radiation pulses are to be transmitted;

determining, by the one or more processors, forward information associated with the forward window based on the information related to the treatment plan, the backward information, and the forward window, the forward information including at least one of a first forward interval of the forward window, a first forward radiation output of the forward window, or a first forward number of pulses of the forward window;

modifying the forward information based on a threshold, the threshold relating to the one or more radiation pulses to be transmitted in the forward window; and determining, by the one or more processors, one or more pulse parameters of the forward window based on the modified forward information.

12. The method of claim 11, wherein the information related to the treatment plan includes at least one of a total time of a treatment, a total radiation during the total time of the treatment, one or more control time points within the total time of the treatment, a radiation output rate associated with each of the one or more control time points within the total time of the treatment, a radiation output per pulse, a cumulative radiation associated with each of the one or more control time points within the total time of the treatment, or an interval between each two neighboring control time points within the total time of the treatment.

13. The method of claim 11, wherein the backward information includes at least one of a backward total radiation of the backward window, a backward cumulative radiation output of the backward window, a backward interval of the backward window, a backward number of pulses in the backward window, or a backward radiation output per pulse of the backward window.

14. The method of claim 13, wherein determining the forward information associated with the forward window based on the information related to the treatment plan, the backward information, and the forward window includes:

determining, by the one or more processors, the first forward interval of the forward window based on the information related to the treatment plan;

determining, by the one or more processors, a forward cumulative radiation output based on the information related to the treatment plan;

determining, by the one or more processors, the first forward radiation output based on the forward cumulative radiation output; and determining, by the one or more processors, the first forward number of pulses in the forward window based on the backward radiation output per pulse and the first forward radiation output.

15. The method of claim 14, wherein modifying the forward information based on the threshold includes:
   determining, by the one or more processors, whether the first forward interval is less than a first threshold; and
   determining, by the one or more processors, whether the first forward radiation output is greater than a second threshold in response to a determination that the first forward interval is greater than or equal to the first threshold.

16. The method of claim 15, wherein modifying the forward information based on the threshold includes:
   determining, by the one or more processors, a second forward radiation output by modifying the first forward radiation output based on the second threshold in response to a determination that the first forward radiation output is greater than the second threshold;
   determining, by the one or more processors, a second forward interval based on the second forward radiation output and the information related to the treatment plan; and
   determining, by the one or more processors, a second forward number of pulses based on the second forward radiation output and the backward radiation output per pulse.

17. The method of claim 15, wherein modifying the forward information based on the threshold includes:
   determining, by the one or more processors, whether the first forward number of pulses is less than a third threshold in response to a determination that the first forward radiation output is less than or equal to the second threshold;
   determining, by the one or more processors, a third forward number of pulses by modifying the first forward number of pulses based on the third threshold in response to a determination that the first forward number of pulses is less than the third threshold; and
   determining, by the one or more processors, a third forward interval based on the third forward number of pulses and the information related to the treatment plan.

18. The method of claim 11, wherein the one or more pulse parameters of the forward window includes at least one of pulse energy, a pulse period, a pulse duty cycle, a pulse shape, or a pulse amplitude.

19. The method of claim 18, wherein determining one or more pulse parameters of the forward window based on the modified forward information includes:
   determining, by the one or more processors, the pulse period of the forward window based on a fourth forward interval and a fourth forward number of pulses.

20. A non-transitory computer readable medium, comprising at least one set of instructions for modulating one or more pulse parameters, wherein when executed by one or more processors, the at least one set of instructions directs the one or more processors to perform acts of:
   obtaining information related to a treatment plan;
   determining a backward window based on the information related to the treatment plan, within which one or more radiation pulses have been transmitted;
   determining backward information associated with the backward window based on the information related to the treatment plan and the backward window;
   determining, based on the information related to the treatment plan, a forward window within which one or more radiation pulses are to be transmitted;
   determining forward information associated with the forward window based on the information related to the treatment plan, the backward information, and the forward window, the forward information including at least one of a first forward interval of the forward window, a first forward radiation output of the forward window, or a first forward number of pulses of the forward window;
   modifying the forward information based on a threshold, the threshold relating to the one or more radiation pulses to be transmitted in the forward window; and
   determining one or more pulse parameters of the forward window based on the modified forward information.

* * * * *